United States Patent
Schulte, II et al.

(10) Patent No.: US 12,338,222 B2
(45) Date of Patent: Jun. 24, 2025

(54) METHOD OF MAKING A BIPHENOL DIANHYDRIDE COMPOSITION, METHOD FOR PURIFICATION OF A BIPHENOL DIANHYDRIDE, AND POLY(ETHERIMIDE)S DERIVED FROM THE BIPHENOL DIANHYDRIDE

(71) Applicant: SHPP GLOBAL TECHNOLOGIES B.V., Bergen op Zoom (NL)

(72) Inventors: James Patrick Schulte, II, Mt. Vernon, IN (US); Dadasaheb V. Patil, Mt. Vernon, IN (US); Juan Justino Rodriguez Ordonez, Cartagena (ES)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 982 days.

(21) Appl. No.: 17/417,241

(22) PCT Filed: Jan. 29, 2020

(86) PCT No.: PCT/US2020/015630
§ 371 (c)(1),
(2) Date: Jun. 22, 2021

(87) PCT Pub. No.: WO2020/160115
PCT Pub. Date: Aug. 6, 2020

(65) Prior Publication Data
US 2022/0073483 A1    Mar. 10, 2022

(30) Foreign Application Priority Data

Jan. 31, 2019 (EP) .................................... 19154911

(51) Int. Cl.
*C07D 307/89*   (2006.01)
*C08G 73/10*    (2006.01)

(52) U.S. Cl.
CPC ....... *C07D 307/89* (2013.01); *C08G 73/1007* (2013.01); *C08G 73/1046* (2013.01); *C08G 73/1071* (2013.01)

(58) Field of Classification Search
CPC .............. C07D 307/89; C08G 73/1007; C08G 73/1046; C08G 73/1071
See application file for complete search history.

(56) References Cited

U.S. PATENT DOCUMENTS

| | | |
|---|---|---|
| 3,879,428 A | 4/1975 | Heath et al. |
| 3,905,942 A | 9/1975 | Takekoshi et al. |
| 3,956,320 A | 5/1976 | Heath et al. |
| 4,293,683 A | 10/1981 | Takekoshi et al. |
| 4,324,882 A | 4/1982 | Takekoshi |
| 4,623,732 A | 11/1986 | Peters |
| 4,808,731 A | 2/1989 | Berdahl et al. |
| 6,727,370 B1 | 4/2004 | Brunelle et al. |
| 7,495,113 B2 | 2/2009 | Pressman et al. |
| 2006/0066004 A1 | 3/2006 | Richards et al. |
| 2007/0073035 A1 | 3/2007 | Stella et al. |
| 2007/0073066 A1 | 3/2007 | Stella et al. |
| 2007/0117990 A1 | 5/2007 | Pressman et al. |
| 2016/0376285 A1 | 12/2016 | Tagami et al. |

FOREIGN PATENT DOCUMENTS

| | | |
|---|---|---|
| CN | 101402625 A | 4/2009 |
| CN | 101696199 B | 9/2011 |
| CN | 106279085 * | 1/2017 |
| CN | 106279085 A | 1/2017 |
| EP | 0593200 A1 | 4/1994 |
| JP | S6299371 A | 5/1987 |
| JP | H07206845 A | 8/1995 |
| JP | 2004196687 A | 7/2004 |
| WO | 2017132656 A1 | 8/2017 |

OTHER PUBLICATIONS

Liu, 2012, Polymer Degradation and Stability, vol. 97, p. 460-468. (Year: 2012).*
Liaw, Chem Mater, 2001 vol. 13, 1811-1816. (Year: 2001).*
International Search Report for the corresponding International Application No. PCT/US2020/015630; Date of Mailing: Jun. 23, 2020; 7 pages.
Takekoshi, T. et al., "Polyetherimides. I. Preparation of Dianhydrides Containing Aromatic Ether Groups", Journal of Polymer Science: Polymer Chemistry Edition, vol. 23, 1985; pp. 1759-1769.
Takekoshi, T. et al., "Polyetherimides. II. High-Temperature Solution Polymerization", Journal of Polymer Science: Polymer Symposium, vol. 74, 1986; pp. 93-108.
Written Opinion for the corresponding International Application No. PCT/US2020/015630; Date of Mailing: Jun. 23, 2020; 11 pages.

(Continued)

*Primary Examiner* — D Margaret M Seaman
(74) *Attorney, Agent, or Firm* — CANTOR COLBURN LLP

(57) ABSTRACT

A method of making a biphenol dianhydride composition includes heating a first solution including a biphenol tetraacid of the formula (I) wherein Ra, Rb, p and q are as defined herein; at least one of sodium ions, potassium ions, calcium ions, zinc ions, aluminum ions, iron ions, phosphate ions, sulfate ions, chloride ions, nitrate ions, and nitrite ions; and a non-halogenated solvent. The N first solution is heated under conditions effective to provide a second solution including the corresponding biphenol dianhydride, the at least one of sodium ions, potassium ions, calcium ions, zinc ions, aluminum ions, iron ions, phosphate ions, sulfate ions, chloride ions, nitrate ions, and nitrite ions, and the non-halogenated solvent.

7 Claims, No Drawings

(56) References Cited

OTHER PUBLICATIONS

Eastmond et al., "A Comparison of Poly(ether imide)s with 3-Phthalimide and 4-Phthalimide Units: Synthesis, Characterization, and Physical Properties," Macromolecules, 2006, pp. 7534-7548, vol. 39.
Liaw et al., "Synthesis and Characterization of New Highly Organosoluble Poly(ether imide)s Bearing a Noncoplanar 2,2'-Dimethyl-4,4'-biphenyl Unit and Kink Diphenylmethylene Linkage," Chem. Mater. 2001, pp. 1811-1816, vol. 13.
JP OA for the corresponding Japanese Application No. 2021-544459; Date of Mailing: Nov. 5, 2024; 7 pages.

\* cited by examiner

METHOD OF MAKING A BIPHENOL DIANHYDRIDE COMPOSITION, METHOD FOR PURIFICATION OF A BIPHENOL DIANHYDRIDE, AND POLY(ETHERIMIDE)S DERIVED FROM THE BIPHENOL DIANHYDRIDE

CROSS REFERENCE TO RELATED APPLICATIONS

This application is a National Stage application of PCT/US2020/015630, filed Jan. 29, 2020, which claims the benefit of European patent application number 19154911.2 filed Jan. 31, 2019, both of which are hereby incorporated by reference in their entirety.

BACKGROUND

Poly(imides), and in particular poly(etherimides) (PEI), are high performance polymers having a glass transition temperature (Tg) of greater 180° C. These polymers further have high strength, heat resistance, and modulus, and broad chemical resistance. Poly(etherimides) are widely used in applications as diverse as automotive and electrical/electronic applications since these compositions offer good mechanical and thermal properties.

Poly(etherimides) can be prepared by condensation polymerization, for example of a dianhydride with a diamine. To obtain good reaction kinetics, achieve high molecular weight, and provide a stable, processable polymer product, high purity monomer components are desirable. Additionally, some applications can require that the polymers have good optical clarity, and good thermal and mechanical properties. The level of haze exhibited by an article can be related to the method by which the polymer is prepared. In practice, it can be difficult to produce the desired dianhydrides that are substantially free of alkali metals and their salts.

Therefore, there is a need in the art for dianhydride monomers that are substantially free of residual phase transfer agents, sodium, potassium, calcium, zinc, aluminum, iron, phosphate, nitrate, nitrite, sulfate, and chloride ions. It would be a further advantage to provide poly(etherimides) that have low levels of such contaminants, and exhibit low haze, high optical clarity, good reaction kinetics during polymerization, high molecular weight, and behave as stable and processable polymers.

SUMMARY

A method of making a biphenol dianhydride composition comprises heating a first solution comprising a biphenol tetraacid of the formula

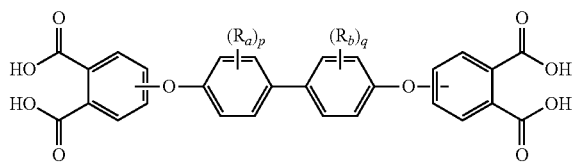

wherein $R^a$ and $R^b$ are each independently a halogen or a monovalent $C_{1-6}$ alkyl group and p and q are each independently an integer of 0 to 4, preferably wherein p and q are each 0; at least one of sodium ions, potassium ions, calcium ions, zinc ions, aluminum ions, titanium ions, phosphorus ions, iron ions, phosphate ions, sulfate ions, chloride ions, nitrate ions, nitrite ions, and sulfite ions; and a non-halogenated solvent comprising ethyl benzoate, diphenyl ether, phenetole, triglyme, benzonitrile, sulfolane, m-cresol, o-cresol, p-cresol, 1-nitrotoluene, 2-nitrotoluene, 3-nitrotoluene, 4-nitrotoluene, N-methyl-pyrrolidinone, 1,3-dimethyl-2-imidazolidinone, sulfolane, dimethyl acetamide, or a combination thereof; under conditions effective to provide a second solution comprising a corresponding biphenol dianhydride, and at least one of sodium ions, potassium ions, calcium ions, zinc ions, aluminum ions, titanium ions, phosphorus ions, iron ions, phosphate ions, sulfate ions, chloride ions, nitrate ions, nitrite ions, and sulfite ions, and the solvent.

A biphenol dianhydride made by the method above is also described.

A poly(etherimide) derived from the biphenol dianhydride and an organic diamine is also described.

A method of making the poly(etherimide) comprises: contacting the biphenol dianhydride with the organic diamine in the presence of an aromatic non-halogenated solvent under conditions effective to provide the poly(etherimide).

An article comprises the poly(etherimide).

The above described and other features are exemplified by the following detailed description.

DETAILED DESCRIPTION

The present inventors have unexpectedly discovered that biphenol dianhydrides can be prepared having low levels of residual contaminants, in particular through the use of a non-halogenated solvent. The present inventors have also discovered a method for preparing the biphenol dianhydride from the corresponding tetraacid precursor using a non-halogenated solvent, and advantageously, the biphenol dianhydride can be used directly for polymerization with a diamine without the need to first isolate the dianhydride. Thus, the biphenol dianhydrides of the present disclosure can also advantageously be used in the preparation of poly(etherimides) having low levels of residual contaminants, affording the polymers with desired properties, in particular good optical clarity and low haze. The poly(etherimides) having a rigid backbone based on a biphenol moiety were found to achieve high molecular weight when prepared using a non-halogenated solvent.

Accordingly, an aspect of the present disclosure is a method for making a biphenol dianhydride composition. The method comprises heating a first solution comprising a biphenol tetraacid, at least one of sodium ions, potassium ions, calcium ions, zinc ions, aluminum ions, iron ions, phosphate ions, sulfate ions, chloride ions, nitrate ions, and nitrite ions; and a non-halogenated solvent.

The biphenol tetraacid has the formula

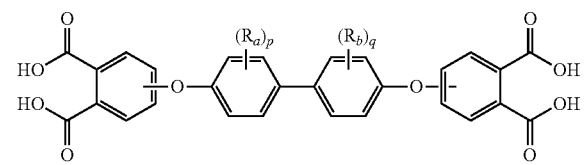

wherein $R^a$ and $R^b$ are each independently a halogen or a monovalent $C_{1-6}$ alkyl group and p and q are each independently an integer of 0 to 4, preferably wherein p and q are each 0. In some embodiments, p, q, or both can be 1 to 4, preferably 1 to 2, more preferably 1. In some embodiments, $R^a$ and $R^b$ can each independently be a $C_{1-3}$ alkyl group, for example a methyl group. The divalent bonds of the biphenol group can be in the 3,3' position, the 3,4' position, or the 4,4' position. Preferably, the divalent bonds of the biphenol group can be in the 3,3' position. The biphenol tetraacid can preferably comprise less than 0.5 weight percent of biphenol as a contaminant.

The non-halogenated solvent is preferably an aromatic non-halogenated solvent. The non-halogenated solvent can comprise ethyl benzoate, diphenyl ether, phenetole, triglyme, benzonitrile, sulfolane, m-cresol, o-cresol, p-cresol, 1-nitrotoluene, 2-nitrotoluene, 3-nitrotoluene, 4-nitrotoluene, N-methyl-pyrrolidinone, 1,3-dimethyl-2-imidazolidinone, dimethyl acetamide, or a combination thereof. In some embodiments, a solvent other than the non-halogenated solvent is excluded from the method. For example, the method can be conducted in the absence of any halogenated solvent. For example, in some embodiments, the method can exclude a halogenated solvent, such as ortho-dichlorobenzene.

The first solution is heated under conditions effective to provide a second solution comprising the corresponding biphenol dianhydride. The biphenol dianhydride can be of the formula

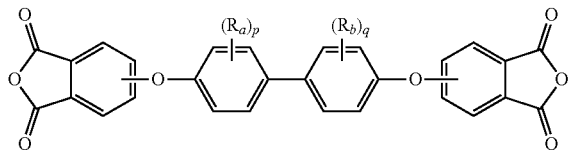

wherein $R^a$, $R^b$, p and q are as defined above. The second solution can further comprise the at least one of sodium ions, potassium ions, calcium ions, zinc ions, aluminum ions, iron ions, phosphate ions, sulfate ions, chloride ions, nitrate ions, nitrite ions, and sulfite ions and the non-halogenated solvent. In some embodiments, the ionic species can comprise one or more inorganic salts, for example, $NaHSO_3$, $Na_2SO_4$, $KHSO_3$, $K_2SO_4$, $NaNO_3$, $NaNO_2$, $KNO_3$, $KNO_2$, NaCl, KCl, $CaSO_4$, and $Ca(NO_3)_2$.

The conditions effective to provide the second solution can include, for example, a temperature of 100 to 200° C., preferably 120 to 180° C., more preferably 150 to 180° C. and a time of 5 minutes to 10 hours, preferably 1 to 10 hours, more preferably 3 to 5 hours. In an aspect, the time to provide the second solution can be less than 5 hours, or less than 4 hours, or less than 3 hours, or 0.5 to less than 5 hours, or 0.5 to 4 hours, or 0.5 to 3 hours, or 0.5 to 2 hours, or 0.5 to 1 hour. The heating can be conducted under pressure, at reduced pressure, or at atmospheric pressure. In some embodiments, the method is preferably conducted in the absence of dehydrating agents such as acetic acid, acetic anhydride, and the like, or a combination thereof. In some embodiments, phase transfer catalysts are excluded from the method.

In an advantageous feature, the method provided herein can exclude the addition of acids. For example, the method does not require the addition of acids such as, but not limited to, hydrochloric acid, acetic acid, formic acid, and the like, or a combination thereof.

In some embodiments, the method can optionally further comprise cooling the second solution to a temperature effective to precipitate the biphenol dianhydride, for example to a temperature of 10 to 70° C., or 25 to 65° C., or 25 to 50° C. and isolating the biphenol dianhydride from the second solution. Isolating the biphenol dianhydride from the second solution can be by, for example, filtration, centrifugation, and the like, or a combination thereof. The isolated biphenol dianhydride can further be washed with a suitable solvent, for example, with a $C_{1-6}$ alcohol, water, or a combination thereof. Preferably, the biphenol dianhydride can be washed with methanol, water, or a combination thereof. In some embodiments, prior to cooling the second solution, the method can further comprise filtering the second solution to remove ionic species. In some embodiments, the filtering can be through a filter having a pore size of 2 micrometers or less. Filtering the second solution can provide a third solution that is of a higher purity than the second solution (i.e., the third solution comprises a reduced amount of ionic species relative to the second solution).

The biphenol dianhydride can be an isomer mixture. For example, 10-100 weight percent of the biphenol dianhydride can have the divalent bonds of the biphenol group of the biphenol dianhydride in the 3,3' position. Preferably, 90-100 weight percent of the biphenol dianhydride can have the divalent bonds of the biphenol group of the biphenol dianhydride in the 3,3' position. Thus, the biphenol dianhydride preferably is an isomer mixture wherein 90 to 100 weight percent of the biphenol dianhydride has the formula

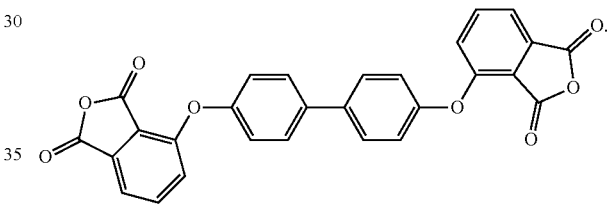

The biphenol dianhydride prepared according to the method described herein can advantageously have low levels of residual contaminants. For example, the biphenol dianhydride can comprise less than 35 ppm each of sodium ions, potassium ions, calcium ions, zinc ions, aluminum ions, and iron ions. The biphenol dianhydride can comprise less than 175 ppm total of sodium ions, potassium ions, calcium ions, zinc ions, aluminum ions, and iron ions. The biphenol dianhydride can comprise less than 30 ppm each of phosphate ions, sulfate ions, chloride ions, nitrate ions, and nitrite ions. The biphenol dianhydride can comprise less than 50 ppm total of phosphate ions, sulfate ions, chloride ions, nitrate ions, and nitrite ions. The biphenol dianhydride can comprise less than 30 ppm each of $NaHSO_3$, $Na_2SO_4$, $KHSO_3$, $K_2SO_4$, $NaNO_3$, $NaNO_2$, $KNO_3$, $KNO_2$, NaCl, KCl, $CaSO_4$, $Ca(NO_3)_2$.

Another aspect of the present disclosure is a method for the purification of a biphenol dianhydride. The method comprises removing an ionic species from a solution comprising a biphenyl dianhydride and a non-halogenated solvent by adsorbing the ionic species from the solution by an adsorbent, by crystallizing the biphenol dianhydride from the solution, by filtering the solution to remove the ionic species, or a combination thereof. The ionic species can be one or more of sodium ions, potassium ions, calcium ions, zinc ions, aluminum ions, iron ions, phosphate ions, sulfate ions, chloride ions, nitrate ions, and nitrite ions. The adsorbent can comprise, for example, celite, diatomaceous earth, silica, alumina, and the like, or a combination thereof. After contacting the biphenol dianhydride solution with the adsorbent, optionally with agitation, the solution can be filtered, preferably through a filter having a pore size of less than 40 to 60 micrometers to provide a solution comprising the biphenol dianhydride and being substantially free of phase-transfer agents, sodium, potassium, calcium, zinc, aluminum, iron, phosphate, nitrate, nitrite, sulfate, or chloride. As used herein, "substantially free" can refer to the solution comprising less than 25 ppm each of phase-transfer agents, sodium, potassium, calcium, zinc, aluminum, iron, phosphate, nitrate, nitrite, sulfate, or chloride. The non-halogenated solvent can be as described above. In some embodiments, the method can further comprise adding an additional solvent having a lower boiling point than the non-halogenated solvent, for example, toluene, xylene, benzene, and the like, or a combination thereof.

Advantageously, the biphenol dianhydride purified according to the above method can possess low levels of residual contaminants and low levels of ionic species. For example, the biphenol dianhydride can comprise less than 35 ppm each of sodium ions, potassium ions, calcium ions, zinc ions, aluminum ions, and iron ions. The biphenol dianhydride can comprise less than 175 ppm total of sodium ions, potassium ions, calcium ions, zinc ions, aluminum ions, and iron ions. The biphenol dianhydride can comprise less than 30 ppm each of phosphate ions, sulfate ions, chloride ions, nitrate ions, and nitrite ions. The biphenol dianhydride can comprise less than 50 ppm total of phosphate ions, sulfate ions, chloride ions, nitrate ions, and nitrite ions.

The biphenol dianhydride made or purified by the methods described herein can advantageously be employed in a method of making a poly(etherimide). The method of making the poly(etherimide) can comprise contacting the biphenol dianhydride with an organic diamine in the presence of a non-halogenated solvent under conditions effective to provide the poly(etherimide).

The biphenol dianhydride can be made or purified according to the methods described herein and therefore advantageously possesses low levels of contaminants. In some embodiments, the biphenol dianhydride can comprise no more than 0.5 weight percent of a biphenol impurity, for example 0 to 0.5 weight percent of a biphenol impurity. In a particularly advantageous feature, the solution comprising the dianhydride can be used directly (i.e., without isolation) in the synthesis of a poly(etherimide).

The organic diamine can include 1,4-butane diamine, 1,5-pentanediamine, 1,6-hexanediamine, 1,7-heptanediamine, 1,8-octanediamine, 1,9-nonanediamine, 1,10-decanediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, o-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(p-amino-t-butyl) toluene, bis(p-amino-t-butylphenyl) ether, bis(p-methyl-o-aminophenyl) benzene, bis(p-methyl-o-aminopentyl) benzene, 1, 3-diamino-4-isopropylbenzene, bis(4-aminophenyl) sulfide, bis-(4-aminophenyl) sulfone (also known as 4,4'-diaminodiphenyl sulfone (DDS)), and bis(4-aminophenyl) ether. Any regioisomer of the foregoing compounds can be used. $C_{1-4}$ alkylated or poly($C_{1-4}$)alkylated derivatives of any of the foregoing can be used, for example a polymethylated 1,6-hexanediamine. Combinations of these compounds can also be used. In some embodiments the organic diamine is m-phenylenediamine, p-phenylenediamine, 4,4'-diaminodiphenyl sulfone, 3,4'-diaminodiphenyl sulfone, 3,3'-diaminodiphenyl sulfone, 4,4'-oxydianiline, 3,4'-oxydianiline, 3,3'-oxydianiline or a combination thereof. In some embodiments, the organic diamine can comprise less than 25 ppm each of sodium ions, potassium ions, calcium ions, zinc ions, aluminum ions, titanium ions, phosphorus ions, and iron ions and less than 30 ppm each of phosphate ions, sulfate ions, chloride ions, nitrate ions, and nitrite ions. In some embodiments, the organic diamine used can comprise less than 30 ppm each of $NaHSO_3$, $Na_2SO_4$, $KHSO_3$, $K_2SO_4$, $NaNO_3$, $NaNO_2$, $KNO_3$, $KNO_2$, $NaCl$, $KCl$, $CaSO_4$, $Ca(NO_3)_2$.

The non-halogenated solvent can comprise benzonitrile, 3-nitrotoluene, m-cresol, p-cresol, N-methyl-pyrrolidinone, sulfolane, and 1,3-dimethyl-2-imidazolidinone, or a combination thereof. In some embodiments, the method excludes any solvent other than the non-halogenated solvent. For example, the method can exclude a halogenated solvent, for example, ortho-dichlorobenzene.

Conditions effective to provide the poly(etherimide) can include a temperature of 170 to 380° C., and a solids content of 1 to 50 weight percent, preferably 20 to 40 weight percent, more preferably 25 to 35 weight percent. Polymerizations can be carried out for 2 to 36 hours, preferably 6 to 16 hours. The polymerization can be conducted at reduced, atmospheric, or high pressure.

In some embodiments, the method can optionally further comprise adding a low-boiling co-solvent to the polymerization. Preferably, the low-boiling solvent is used to remove water from the polymerization reaction by azeotropic distillation. Suitable low-boiling co-solvents can include, for example, toluene, benzene, xylene, and the like or a combination thereof.

The method can also optionally employ various chain stoppers or end capping agents, and thus the poly(etherimide) can optionally further comprise at least one chain end derived from a chain stopper. The chain stopper limits molecular weight growth rate and thus can be used to control molecular weight in the poly(etherimide). Exemplary chain stoppers include certain mono amines (for example aniline), mono anhydrides (for example phthalic anhydride), monophenolic compounds and the like. In some embodiments, the chain stopper can preferably be a monoamine chain stopper or a monoanhydride chain stopper, more preferably aniline or phthalic anhydride. It should be understood however that the poly(etherimides) disclosed herein can be produced having any desired weight average molecular weight (Mw) with any end cap.

In some embodiments, the organic diamines, the chain stoppers (when present), or both can possess low levels of inorganic contaminants, for example less than 50 ppm or less than 25 ppm each of phosphate ions, sulfate ions, chloride ions, nitrate ions, and nitrite ions and less than 50 ppm or less than 35 ppm each of sodium ions, potassium ions, zinc ions, calcium ions, aluminum ions, iron ions, and phosphorus ions.

In some embodiments, no catalysts are used in the polymerization of the poly(etherimide).

Advantageously, the polymerization conducted according to the present disclosure can remain homogenous throughout the entire course of the polymerization method. This can facilitate the preparation of high molecular weight polymers. In some embodiments, the poly(etherimide) can have a weight average molecular weight of greater than 25,000 grams per mole, for example greater than 25,000 to 35,000 grams per mole. Molecular weight can be determined using gel permeation chromatography (GPC) relative to polystyrene standards, as further described in the working examples below.

The method of making the poly(etherimide) can optionally further comprise a devolatilization step. Low levels of residual volatile species in the final polymer product can be achieved by devolatilization, and devolatilization can also serve to finish the end groups in the polymer product. In some embodiments the bulk of any solvent may be removed, and any residual volatile species may be removed from the polymer product by devolatilization, optionally at reduced pressure. In other embodiments the polymerization reaction is taken to some desired level of completion in solvent and then the polymerization is essentially completed during at least one devolatilization step following the initial reaction in solution. Apparatuses to devolatilize the polymer mixture and reduce solvent and other volatile species to the low levels needed for good melt processability are generally capable of high temperature heating under vacuum with the ability to rapidly generate high surface area to facilitate removal of the volatile species. The mixing portions of such apparatuses are generally capable of supplying sufficient power to pump, agitate and stir the high temperature, amorphous polyphenylene ether sulfone and poly(etherimide) melt which may be very viscous. Suitable devolatilization apparatuses include, but are not limited to, wiped films evaporators and devolatilizing extruders, especially twin-screw extruders with multiple venting sections. In some embodiments, the method can optionally further comprise devolatilizing the poly(etherimide) at 360 to 390° C. for 1 to 30 minutes.

The poly(etherimide) prepared according to the method described herein and using the biphenol dianhydride made or purified according to the present disclosure can advantageously have low levels of residual impurities. In particular, the poly(etherimide) can comprise less than 25 ppm each of sodium ions, potassium ions, calcium ions, zinc ions, aluminum ions, and iron ions and less than 30 ppm each of phosphate ions, sulfate ions, chloride ions, nitrate ions, and nitrite ions.

Poly(etherimides) prepared according to the method of the present disclosure can be particularly useful for forming various articles. The poly(etherimide) can be formed into articles using a suitable technique, for example, melt-processing techniques. Melt-molding methods can include injection molding, extrusion molding, blow molding, rotational molding, coining, and injection blow molding. For example, the melt molding method can be injection molding. The poly(etherimide) can be formed into sheets or films by casting, blowing, or extruding. These can be further thermoformed into articles and structures that can be oriented from the melt or at a later stage in the processing of the compositions. The poly(etherimide) can be over-molded onto an article made from a different material or by a different process. The articles can also be formed using techniques such as compression molding or ram extruding. The articles can be further formed into other shapes by machining. Exemplary articles include a fiber, a film, a sheet, a foam, a filament, a molded article, an extruded article, or a powder. The poly(etherimide) of the present disclosure can also be particularly suitable for use in optoelectronic applications. In particular, the poly(etherimide) can be used for optoelectronic articles such as transmitters, receivers, connectors, lenses, waveguides, and the like.

Accordingly, methods for the preparation and purification of a biphenol dianhydride having low levels of residual contaminants are provided herein. The biphenol dianhydrides of the present disclosure can be used in the preparation of rigid, high molecular weight biphenyl-containing poly(etherimides) which can be particularly useful for various applications, for example in optical articles. Thus, a significant improvement is provided by the present disclosure.

This disclosure is further illustrated by the following examples, which are non-limiting.

EXAMPLES

Materials used in the following examples are described in Table 1.

TABLE 1

| Material | Chemical Description |
| --- | --- |
| 3,3'-BPoTA | 3,3'-biphenol diphthalic acid (3,3'-biphenol tetraacid) |

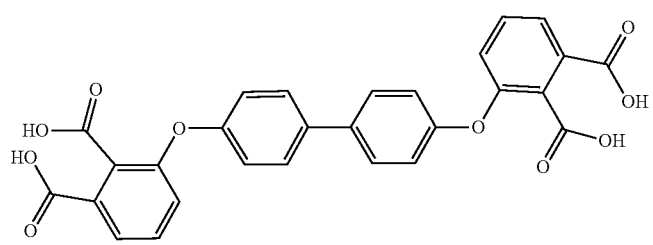 [SMILES: O=C(O)c1cccc(Oc2ccc(-c3ccc(Oc4cccc(C(=O)O)c4C(=O)O)cc3)cc2)c1C(=O)O]

TABLE 1-continued

| Material | Chemical Description |
|---|---|
| 3,4'-BPoTA | 3,4'-biphenol diphthalic acid (3,4'-biphenol tetraacid) |
| 4,4'-BPoTA | 4,4'-biphenol diphthalic acid (4,4'-biphenol tetraacid) |
| 3,3'-BPoDA | 3,3'-biphenol diphthalic anhydride |
| 3,4'-BPoDA | 3,4'-biphenol diphthalic anhydride |
| 4,4'-BPoDA | 4,4'-biphenol diphthalic anhydride |

TABLE 1-continued

| Material | Chemical Description |
|---|---|
| BPoAnhDA | Biphenol anhydride diacid |

[Chemical structure: Biphenol anhydride diacid showing a phthalic anhydride group connected through an ether linkage to a biphenyl group, connected through another ether linkage to a phenyl group bearing two CO₂H groups]

| | |
|---|---|
| 4,4'-DDS | 4,4'-Diaminodiphenyl sulfone |
| p-PD | Para-phenylene diamine |
| 4,4'-ODA | 4,4'-Oxydianiline |
| m-PD | Meta-phenylene diamine |
| PA | Phthalic Anhydride |
| o-DCB | Ortho-dichlorobenzene |
| DI Water | Deionized water |
| o-xylene | Ortho-xylene |
| NMP | 1-Methyl-2-pyrrolidone |
| DMZ | 1,3-dimethyl-2-imidazolidinone |
| m-cresol | Meta-cresol |
| p-cresol | Para-cresol |
| DMA | N,N-dimethylacetamide |
| DMSO | Dimethylsulfoxide |
| Sulfolane | Tetramethylene sulfone |
| phenetole | Ethyl phenyl ether |
| Triglyme | Triethylene glycol dimethyl ether |

All polymer molecular weights in the following examples are determined by gel permeation chromatography (GPC) analysis with a Water 2695 Separations Module equipped with a Polymer Lab Plgel 5 micrometer MIXED-C column and Waters 2487 PDA detector at 254 nm. Elution was effected with an isocratic solvent system of dichloromethane at 1 mL/min and polymer molecular weights were reported with respect to polystyrene standards unless otherwise noted.

All ultra-performance liquid chromatography (UPLC) analyses in the following examples were performed on a Waters ACQUITY UPLC BEH C18 1.7 μm 2.1×50 mm column at 35° C. PDA detection was performed at 254 nm with a flow rate of 0.313 mL/min. A gradient method was used with a dual solvent system of acetonitrile and acidic water (4 L DI $H_2O$+3 mL 85% $H_3PO_4$). It is noted that UPLC analysis of BPoDA shows small amounts of BPoAnhydride-Diacid ("BPoAnhDA") due to partial hydrolysis that occurs during analysis.

All residual levels of metals (sodium, potassium, zinc, calcium, aluminum, iron, titanium, phosphorus) in the following examples are determined by an inductively coupled plasma-digestion (ICP-Dig) method which uses an ICP spectrometer equipped with: an axial and/or radial viewing, a Gem Cone and/or Ultrasonic nebulizer, and a microwave digestion system equipped with appropriate sample digestion vessels set. Samples are prepared using concentrated nitric acid, hydrochloric acid, sulfuric acid, and/or hydrofluoric acid—Supra pure grades.

Residual levels of anions (sulfates, chlorides, phosphates, nitrates, nitrites) present in BPoDA and poly(etherimide) samples were measured by extraction-ion chromatography (IC-Extract). The BPoDA samples were dissolved in methylene chloride and the poly(etherimide) samples were dissolved in methylene chloride with hexafluroroisopropanol (HFIP) added to help with solubility. The solutions were then extracted with deionized water, and then the aqueous extracts were analyzed using a calibrated Dionex ICS 2000 instrument.

Residual levels of anions (sulfates, chlorides, phosphates, nitrates, nitrites) present in BPoTA samples were measured by total ion chromatography combustion (IC-Total) using a calibrated Dionex ICS 2000 instrument.

The following example 1 used BPoTA which had the following profile: ICP-Dig: sodium (534 ppm), potassium (12.6 ppm), zinc (14 ppm), calcium (19 ppm), aluminum (217 ppm), iron (527 ppm), titanium (5.7 ppm), phosphorus (7.8 ppm), nickel (182 ppm); UPLC: 3,3'-BPoTA and isomers (97.8%).

Comparative Example 1

To a 250 mL 3-neck round-bottom flask with mechanical stirrer, Dean-Stark trap and condenser, 3,3'-BPoTA (6 g, 11.66 mmol), toluene (100 g, 103 mL) and acetic anhydride (8.70 g, 8 ml) were added. The mixture was then heated to 140° C. under nitrogen in an oil bath. The fresh toluene was added to the reaction flask to make up the solvent loss in the Dean-Stark trap. After 9 hours, UPLC analysis indicated the reaction was complete and a light-gray colored precipitate in toluene was observed. The mixture was then cooled to room temperature. The product was collected by filtration and then washed with hot DI water (2×20 mL). The product was allowed to dry in the vacuum oven at 140-145° C. until a consistent mass was obtained. In this manner, 3.18 g of the 3,3'-BPoDA product was collected in 56.9% yield. UPLC: BPoDA isomers (97%); ICP-Dig: sodium (511 ppm), potassium (8.7 ppm), zinc (5.3 ppm), calcium (18.5 ppm), aluminum (12.9 ppm), iron (15.4 ppm), titanium (0 ppm), phosphorus (24 ppm).

The following examples 2-10 used the BPoTA which had the following profile: ICP-Dig: sodium (138 ppm), potassium (9 ppm), zinc (2 ppm), calcium (6 ppm), aluminum (2 ppm), iron (20 ppm), titanium (0 ppm), phosphorus (7 ppm); IC-Total: sulfates (278.8 ppm), phosphates (2.4 ppm), chlorides (1.2 ppm), fluoride (3 ppm), nitrite (1.5 ppm), nitrates (<0.5 ppm)); UPLC: 3,3'-BPoTA and isomers (98.50%).

Comparative Example 2

To a 250 mL 3-neck round-bottom flask with mechanical stirrer, Dean-Stark trap and condenser, 3,3'-BPoTA (30 g, 58.31 mmol), acetic acid (55 g, 52 mL) and acetic anhydride (55 g, 51 mL) were added. The flask was then placed in an oil bath and heated to 130° C. under nitrogen. After 5-6 hours, UPLC analysis indicated the reaction was complete and a light gray colored precipitate in solvent mixture was observed. The mixture was then cooled to room temperature. The product was collected by filtration and then washed with hot DI water (2×35 mL). The product was allowed to dry in the vacuum oven at 140-145° C. until a consistent mass was obtained. In this manner, 22.60 g (81% yield) of the 3,3'-BPoDA product was collected. UPLC: BPoDA isomers (97.8%); ICP-Dig: sodium (5 ppm), potassium (12 ppm), zinc (1 ppm), calcium (13 ppm), aluminum (4 ppm), iron (11 ppm), titanium (0 ppm), phosphorus (6 ppm); IC-Extract: sulfates (21.0 ppm), chloride (<0.5 ppm), phosphates (1.6 ppm), nitrates (<0.5 ppm), nitrites (<0.5 ppm).

Example 3

In a 250 mL 3-neck round-bottom flask with mechanical stirrer, Dean-Stark trap and condenser was placed above 3,3'-BPoTA (15 g, 29.15 mmol) and NMP (56 g, 55 mL). The flask was then placed in an oil bath at 160° C. under nitrogen. The fresh NMP was added to the reaction flask to make up the solvent loss in the Dean-Stark trap. After 3-4 hours, UPLC analysis indicated the reaction was complete. The mixture was then cooled to 50° C. To homogenous solution of 3,3'-BPoDA in NMP, DI water (100 mL) was added to form an orange colored precipitate. The product was collected by filtration and then washed with methanol (50° C., 3×20 mL), followed up by DI water (60-70° C., 2×20 mL). The product was allowed to dry in the vacuum oven at 140-145° C. until a consistent mass was obtained. In this manner, 13.37 g of the 3,3'-BPoDA product was collected in 95.90% yield. UPLC: BPoDA isomers (98.99%); ICP-Dig: sodium (33 ppm), potassium (15 ppm), zinc (3 ppm), calcium (22 ppm), aluminum (4 ppm), iron (22 ppm), titanium (0 ppm), phosphorus (7 ppm); IC-Extract: sulfates (3 ppm), phosphates (<0.5 ppm), nitrites (<0.5 ppm), nitrates (<0.5 ppm), chlorides (<0.5 ppm), fluorides (0.8 ppm).

Example 4

To a 250 mL 3-neck round-bottom flask with mechanical stirrer, Dean-Stark trap and condenser, 3,3'-BPoTA (15 g, 29.15 mmol) and DMZ (56 g, 53 mL) was added. The flask was then placed in an oil bath at 160° C. under nitrogen. Fresh DMZ was added to the reaction flask to make up the solvent loss in the Dean-Stark trap. After 3-4 hours, UPLC analysis indicated the reaction was complete. The mixture was then cooled to 50° C. to form a pale white colored precipitate in DMZ. The product was collected by filtration and then washed with methanol (50° C., 3×20 mL), followed up by DI water (60-70° C., 2×20 mL). The product was allowed to dry in the vacuum oven at 140-145° C. until a consistent mass was obtained. In this manner, 11.82 g of the 3,3'-BPoDA product was collected in 84.80% yield. UPLC: BPoDA isomers (99.15%); ICP-Dig: sodium (10 ppm), potassium (28 ppm), zinc (0 ppm), calcium (6 ppm), aluminum (4 ppm), iron (7 ppm), titanium (0 ppm), phosphorus (8 ppm); IC-Extract: sulfates (1.5 ppm), phosphates (<0.5 ppm), nitrites (6.1 ppm), nitrates (<0.5 ppm), chlorides (<0.5 ppm), fluorides (1.2 ppm).

Example 5

To a 250 mL 3-neck round-bottom flask with mechanical stirrer, Dean-Stark trap and condenser, 3,3'-BPoTA (15 g, 29.15 mmol) and m-cresol (56 g, 54 mL) was added. The flask was then placed in an oil bath at 160° C. under nitrogen. The fresh m-cresol was added to the reaction flask to make up the solvent loss in the Dean-Stark trap. After 3-4 hours, UPLC analysis indicated the reaction was complete. The mixture was then cooled to 50° C. to form an off-white colored precipitate in m-cresol. The product was collected by filtration and then washed with methanol (50° C., 3×20 mL), followed up by DI water (60-70° C., 2×20 mL). The product was allowed to dry in the vacuum oven at 140-145° C. until a consistent mass was obtained. In this manner, 12.31 g of the 3,3'-BPoDA product was collected in 88.26% yield. UPLC: BPoDA isomers (98.70%); ICP-Dig: sodium (15 ppm), potassium (13 ppm), zinc (3 ppm), calcium (15 ppm), aluminum (2 ppm), iron (5 ppm), titanium (0 ppm), phosphorus (8 ppm); IC-Extract: Sulfates (4.3 ppm), phosphates (<0.5 ppm), nitrites (<0.5 ppm), nitrates (<0.5 ppm), chlorides (<0.5 ppm), fluorides (1.3 ppm).

Example 6

To a 250 mL 3-neck round-bottom flask with mechanical stirrer, Dean-Stark trap and condenser, 3,3'-BPoTA (15 g, 29.15 mmol) and benzonitrile (56 g, 56 mL) was added. The flask was then placed in an oil bath at 160° C. under nitrogen. The fresh benzonitrile was added to the reaction flask to make up the solvent loss in the Dean-Stark trap. After 3-4 hours, UPLC analysis indicated the reaction was complete. The mixture was then cooled to 50° C. to form a light off-white precipitate in benzonitrile. The product was collected by filtration and then washed with methanol (50° C., 2×30 mL), followed up by DI water (60-70° C., 2×20 mL). The product was allowed to dry in the vacuum oven at 140-145° C. until a consistent mass was obtained. In this manner, 12.67 g of the 3,3'-BPoDA product was collected in 90.80% yield. UPLC: BPoDA isomers (99.16%); ICP-Dig: sodium (9 ppm), potassium (14 ppm), zinc (2 ppm), calcium (7 ppm), aluminum (3 ppm), iron (59 ppm), titanium (0 ppm), phosphorus (11 ppm); IC-Extract: sulfates (5.1 ppm), phosphates (<0.5 ppm), nitrites (<0.5 ppm), nitrates (<0.5 ppm), chlorides (<0.5 ppm), fluorides (<0.5 ppm).

Example 7

To a 1000 mL 3-neck round-bottom flask with mechanical stirrer, Dean-Stark trap and condenser, 3,3'-BPoTA (60 g, 116.63 mmol) and benzonitrile (504 g, 504 mL) was added. The flask was then placed in an oil bath at 160° C. under nitrogen. The fresh benzonitrile was added to the reaction flask to make up the solvent loss in the Dean-Stark trap. After 3 hours, UPLC analysis indicated the reaction was complete. The homogenous solution was then heated to 170° C. The solution was transferred to Mott filter (pre-heated to 170° C., filter media of 2 micron) and the solution was then maintained at this temperature for 15-20 minutes, followed by filtration under pressure (10-20 psig) to collect the BPoDA solution in benzonitrile. UPLC: BPoDA isomers (98.90%); Metal/anions profile post Mott filtration: ICP-Dig: sodium (7 ppm), potassium (14 ppm), zinc (2 ppm), calcium (9 ppm), aluminum (0 ppm), iron (4 ppm), titanium (0 ppm), phosphorus (8 ppm), chromium (1 ppm), copper (0 ppm), nickel (0 ppm), magnesium (0 ppm), manganese (0 ppm); IC-Extract: sulfates (12 ppm), phosphates (<0.5 ppm), nitrites (<0.5 ppm), nitrates (<0.5 ppm), chlorides (<0.5 ppm), fluorides (<0.5 ppm), bromide (<0.5 ppm).

Example 8

The solution from above (example 7) was then concentrated to 15-20 wt % solids and cooled to 50° C. to form a light off-white precipitate in benzonitrile. The product was collected by filtration and then washed with methanol (50° C., 3×35 mL), followed up by DI water (60-70° C., 2×50 mL). The product was allowed to dry in the vacuum oven at 140-145° C. until a consistent mass was obtained. In this manner, 37.94 g of the 3,3'-BPoDA product was collected in 68% yield. Metal/anions profile isolated DA: UPLC: BPoDA isomers (99.30%); ICP-Dig: sodium (7 ppm), potassium (17 ppm), zinc (2 ppm), calcium (11 ppm), aluminum (0 ppm), iron (1 ppm), titanium (0 ppm), phosphorus (7 ppm), chromium (1 ppm), copper (0 ppm), magnesium (0 ppm), nickel (0 ppm), manganese (0 ppm); IC-Extract: sulfates (12.1 ppm), phosphates (<0.5 ppm), nitrites (<0.5 ppm), nitrates (<0.5 ppm), chlorides (<0.5 ppm), fluorides (<0.5 ppm), bromide (<0.5 ppm).

The following example 9 used BPoDA which had the following profile: ICP-Dig: sodium (157 ppm), potassium (<10 ppm), zinc (12.2 ppm), calcium (12.9 ppm), aluminum (7.2 ppm), iron (20.8 ppm), titanium (<1 ppm), phosphorus (0 ppm); IC-Extract: sulfates (314.6), chlorides (1.3), nitrates (<0.5), nitrites (<0.5), phosphates (<0.5); UPLC: 3,3'-BPoDA (92.15%), BPoAnhDA (7.47%).

Example 9

To a 100 mL 3-neck round-bottom flask with magnetic stir bar, Dean-Stark trap and condenser was charged a mixture of crude 3,3'-BPoDA (1.5 g, 3.13 mmol) and m-cresol (15 mL). The flask was heated to 200° C. and then the solution was quickly transferred to a preheated (150° C.) glass syringe affixed with a 0.45 micrometer PTFE filter. The solution was filtered onto a watch glass and the solvent was removed on a hot plate in a fume hood until the solid dianhydride was dry. UPLC: 3,3'-BPoDA+BPoAnhDA (100%); ICP-Dig: sodium (23.4 ppm), potassium (<10 ppm), zinc (16.3 ppm), calcium (17.8 ppm), aluminum (7.9 ppm), iron (12.5 ppm), titanium (<1 ppm), phosphorus (0 ppm); IC-Extract: sulfates (<0.5), chlorides (1.3), nitrates (<0.5), nitrites (<0.5), phosphates (<0.5).

Example 10

A 1 L round-bottomed flask was charged with 3,3'-BPoTA (20.08 g) and m-cresol (168 g). The mixture was stirred at 150 rpm with an overhead stirrer and heated to 180° C. Once the UPLC showed complete disappearance of BPoTA peak, the reaction mixture maintained at 180° C. for additional 30 minutes. A coarse fritted glass filter funnel was then prepared with three inches of Celite 545. The 3,3'-BPoDA solution was then filtered through the Celite using vacuum at 180° C. The filtrate was then passed through the Celite a second time and then allowed to cool to ambient temperature. The resulting 3,3'-BPoDA solids were collected on a #4 Whatman filter paper. The cake solids were washed with MeOH (2×50 mL) followed by DI water (2×50 mL). The purified 3,3'-BPoDA was then dried in a vacuum oven at 90° C. until a consistent mass was obtained to provide the dianhydride as a white solid in 5.46 g (29.24% yield). UPLC: BPoDA isomers+BPoAnhDA (98.91%); ICP-Dig: sodium (31.3 ppm), potassium (6.98 ppm), zinc (5.34 ppm), calcium (11.3 ppm), aluminum (4.34 ppm), iron (7.78 ppm), titanium (<1 ppm), phosphorus (<1 ppm); IC-Extract: sulfates (15.1 ppm), phosphates (<0.5 ppm), nitrites (<0.5 ppm), nitrates (<0.5 ppm), chlorides (5.4 ppm).

A variety of conditions were used to determine which were most effective in the purification of BPoDA from organic and inorganic contaminants. The different conditions evaluated included the use of different organic solvents/reagents followed by purification step, which involved either crystallization, Mott filtration, Mott filtration followed by crystallization, filtration alone or filtration through the application of adsorbents (like Celite) followed by crystallization. The results are summarized in Table 2, which shows that cyclization of BPoTA to BPoDA in non-halogenated solvents such as NMP, DMZ, m-cresol and benzonitrile provide homogeneous solutions, which were purified using the above methods to yield a dianhydride having high purity and very low levels of inorganic contaminants particularly sodium ions and sulfate ions. Further, use of these solvents allowed higher weight percent solids, which will help, achieve higher throughput and improved efficiency. On the other hand, comparative examples involving use of low boiling toluene and acetic acid/acetic anhydride formed a slurry even at lower weight percent solids. Further, the use of toluene (Example 1) afforded the dianhydride product in very high levels of sodium ions among others. When acetic acid and acetic anhydride mixture was used (Example 2), the resultant product showed lower levels of metal ions and sulfate. However, this method involves use of highly corrosive chemicals. Further, the presence of residual amounts these chemicals will adversely affect polymerization step, not allowing to build high molecular weight. The use of non-halogenated solvents in combination with different methods of purifications found to perform very effectively.

TABLE 2

| | BPoTA | | | BPoDA | | |
|---|---|---|---|---|---|---|
| Example | Sodium (initial) | Sulfate (initial) | Solvent | Purification Conditions | Sodium (final) | Sulfate (final) |
| 1* | 534 | ND | toluene/acetic anhydride | crystallization | 511 | ND |
| 2* | 138 | 278 | acetic acid/acetic anhydride | crystallization | 5 | 21 |
| 3 | 138 | 278 | NMP | crystallization | 33 | 5 |
| 4 | 138 | 278 | DMZ | crystallization | 10 | 1.5 |
| 5 | 138 | 278 | m-cresol | crystallization | 15 | 4.3 |
| 6 | 138 | 278 | benzonitrile | crystallization | 9 | 5.1 |
| 7 | 138 | 278 | benzonitrile | Mott filtration | 9 | 12 |

TABLE 2-continued

| | BPoTA | | | BPoDA | | |
|---|---|---|---|---|---|---|
| Example | Sodium (initial) | Sulfate (initial) | Solvent | Purification Conditions | Sodium (final) | Sulfate (final) |
| 8 | 138 | 278 | benzonitrile | 1. Mott filtration 2. crystallization | 7 | 12.1 |
| 9 | 157** | 315** | m-cresol | filtration | 23.4 | <0.5 |
| 10 | 138 | 278 | m-cresol | 1. Celite 2. crystallization | 31.3 | 15.1 |

*denotes Comparative Examples
**From BPoDA starting material

The following examples describe the preparation of poly(etherimide) in non-halogenated solvent. Examples 11-26 used 3,3'-BPoDA which had the following profile: ICP-Dig: sodium (5 ppm), potassium (41 ppm), zinc (2 ppm), calcium (4 ppm), aluminum (3 ppm), iron (9 ppm), titanium (0 ppm), phosphorus (10 ppm); IC-Extract: sulfates (4.6 ppm), chloride (<0.5 ppm), phosphates (<0.5 ppm), nitrates (<0.5 ppm), nitrites (<0.5 ppm); UPLC: 3,3'-BPoDA (96.26%), BPoAnhDA (3.74%).

Examples 11-26 used m-PD which had the following profile: ICP-Dig: sodium (1 ppm), potassium (12 ppm), zinc (0 ppm), calcium (3 ppm), aluminum (3 ppm), iron (0 ppm), titanium (0 ppm), phosphorus (5 ppm); IC-Extract: sulfates (<0.5 ppm), chloride (130.7 ppm), phosphates (<0.5 ppm), nitrates (1.9 ppm), nitrites (<0.5 ppm).

Example 11

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), phthalic anhydride (0.726 g, 4.90 mmol), m-PD (2.70 g, 25.0 mmol), 4,4'-DDS (5.08 g, 20.5 mmol), and benzonitrile (109 g) was added. The flask was placed in an oil bath at 25° C. and began to heat to 200° C. oil bath with an agitation of 150-200 rpm.

After 23 minutes the oil bath temperature reached 140° C. and a glue-ball stage (containing a biphasic mixture with a solid mass of prepolymer) was observed, whereupon agitation was reduced to 80-100 rpm. After an additional four minutes, the oil bath temperature reached 148° C. and the mixture became a homogenous yellow-orange solution whereupon agitation was increased to 200 rpm. The target oil bath temperature of 200° C. was obtained within 40-45 minutes of heating. After a total of two hours and 45 minutes, 46 g of distillate was removed from the trap to give a 30 wt % solids solution and then the nitrogen sweep was reduced to 0.5 scfh. After a total of seven hours the homogenous yellow-orange polymer solution was poured into a foil pan and cooled to ambient temperature. A sample was devolatilized (using a hot block) for 20 minutes at 380-385° C. under nitrogen. ICP-Dig: sodium (14), potassium (14 ppm), zinc (12 ppm), calcium (14 ppm), aluminum (11 ppm), iron (8 ppm), titanium (0 ppm), phosphorus (16 ppm); IC-Extract: sulfates (10.7 ppm), chlorides (3 ppm), phosphates (<0.5 ppm), nitrates (<0.5 ppm), nitrites (<0.5 ppm).

Example 12

In a 250 mL 3-neck round bottom flask affixed with a Dean-Stark trap, condenser, mechanical stirrer, and nitrogen inlet (2 scfh) was added 3,3'-BPoDA (20.81 g, 43.49 mmol), m-PD (2.70 g, 25.0 mmol), 4,4'-DDS (5.08 g, 20.5 mmol), and benzonitrile (109 g). The flask was placed in an oil bath at 25° C. and began to heat to 200° C. oil bath with an agitation of 120-150 rpm.

After 18 minutes, the oil bath temperature reached 159° C. and a glue ball stage (containing a biphasic mixture with a solid mass of prepolymer) was observed. After an additional two minutes, the temperature rose to 169° C. and a homogenous yellow solution was obtained. At this point, the agitation was increased to 200 rpm. After a total of 60 minutes of heating, the target oil bath temperature of 200° C. was achieved and 46 g of distillate was removed from the trap to provide reaction mixture at 30 wt % solids. The nitrogen sweep was reduced to 0.5 scfh. After a total of two hours and ten minutes, PA (0.726 g, 4.90 mmol) and benzonitrile (10 mL) was added to the mixture and the nitrogen flow was increased. After an additional 40 minutes, 13 g of distillate was removed from the trap and the nitrogen flow was reduced to 0.5 scfh. After a total of seven hours and 30 minutes of heating, a large sample was removed and devolatilized (hot block) for 20 minutes at 380-385° C. under nitrogen. GPC: weight average MW=28,005 grams per mole; Mn=13,348 grams per mole; PDI=2.10; Mz/Mw=1.35; DSC (Tg)=280.6° C.

The remainder of the polymer solution was heated for a total of 24.5 hrs and then poured into a foil pan and cooled to ambient temperature. A sample was devolatilized (using a hot block) for 20 minutes at 380-385° C. under nitrogen. GPC: weight average MW=28,401 grams per mole; Mn=13,566 grams per mole; PDI=2.09; Mz/Mw=1.36. ICP-Dig: sodium (5.1), potassium (7.1 ppm), zinc (22.7 ppm), calcium (9.9 ppm), aluminum (<0.1 ppm), iron (<0.1 ppm), titanium (0 ppm), phosphorus (11 ppm); IC-Extract: sulfates (6.5 ppm), chlorides (7.6 ppm), phosphates (<0.5 ppm), nitrates (<0.5 ppm), nitrites (<0.5 ppm); DSC (Tg)=278.6° C.

Example 13

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), m-PD (2.70 g, 25.0 mmol), 4,4'-DDS (5.08 g, 20.5 mmol), and 3-nitrotoluene (109 g) were added. The flask was placed in an oil bath at 25° C. and began to heat to 200° C. oil bath with an agitation of 150-200 rpm.

After 22 minutes, the oil bath temperature reached 178° C. and a glue-ball stage (containing a biphasic mixture with a solid mass of prepolymer) was observed, whereupon agitation was reduced to 100-120 rpm. Within a few minutes, the oil bath temperature reached 181° C. and the mixture became a homogenous orange solution whereupon agitation was increased to 200 rpm. The target oil bath temperature of 200° C. was obtained within 40-45 minutes of heating. After a total of three hours, 46 g of distillate was removed from the trap to give a 30 wt % solids solution and then the nitrogen sweep was reduced to 0.5 scfh. After a total of seven hours the homogenous orange polymer solution was poured into a foil pan and cooled to ambient temperature. A sample was devolatilized (using a hot block) for 20 minutes at 380-385° C. under nitrogen. ICP-Dig: sodium (8), potassium (6 ppm), zinc (27 ppm), calcium (12 ppm), aluminum (4 ppm), iron (9 ppm), titanium (0 ppm), phosphorus (12 ppm); IC-Extract: sulfates (8.8 ppm), chlorides (<0.5 ppm), phosphates (<0.5 ppm), nitrates (2 ppm), nitrites (<0.5 ppm).

Example 14

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), phthalic anhydride (0.726 g, 4.90 mmol), m-PD (2.70 g, 25.0 mmol), 4,4'-DDS (5.08 g, 20.5 mmol), and p-cresol (109 g) were added. The flask was placed in an oil bath at 25° C. and began to heat to 200° C. oil bath with an agitation of 120 rpm.

After 22 minutes, the oil bath temperature reached 147° C. and the mixture became a homogenous yellow solution whereupon agitation was increased to 200 rpm. The target oil bath temperature of 200° C. was obtained within 45 minutes of heating. After an additional 75 minutes, 46 g of distillate was removed from the trap to give a 30 wt % solids solution and then the nitrogen sweep was reduced to 0.5 scfh. After a total of seven hours and 35 minutes, the homogenous yellow polymer solution was poured into a foil pan and cooled to ambient temperature. A sample was devolatilized (using a hot block) for 20 minutes at 380-385° C. under nitrogen. ICP-Dig: sodium (11.9), potassium (10.8 ppm), zinc (9.1 ppm), calcium (15.3 ppm), aluminum (20.9 ppm), iron (11.5 ppm), titanium (3.9 ppm), phosphorus (11 ppm); IC-Extract: sulfates (16 ppm), chlorides (<0.5 ppm), phosphates (<0.5 ppm), nitrates (4.3 ppm), nitrites (<0.5 ppm).

Example 15

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), phthalic anhydride (0.726 g, 4.90 mmol), m-PD (2.70 g, 25.0 mmol), 4,4'-DDS (5.08 g, 20.5 mmol), and m-cresol (109 g) were added. The flask was placed in an oil bath at 25° C. and began to heat to 200° C. oil bath with an agitation of 150-200 rpm.

After 27 minutes, the oil bath temperature reached 135° C. and the mixture became a homogenous orange solution whereupon agitation was increased to 200 rpm. The target oil bath temperature of 200° C. was obtained within 40-45 minutes of heating. After a total of three hours, 46 g of distillate was removed from the trap to give a 30 wt % solids solution and then the nitrogen sweep was reduced to 0.5 scfh. After a total of seven hours the homogenous orange polymer solution was poured into a foil pan and cooled to ambient temperature. A sample was devolatilized (using a hot block) for 20 minutes at 380-385° C. under nitrogen. ICP-Dig: sodium (20), potassium (13 ppm), zinc (20 ppm), calcium (26 ppm), aluminum (11 ppm), iron (11 ppm), titanium (0 ppm), phosphorus (14 ppm); IC-Extract: sulfates (7.6 ppm), chlorides (2.8 ppm), phosphates (<0.5 ppm), nitrates (<0.5 ppm), nitrites (<0.5 ppm).

Example 16

In a 500 mL 3-neck round bottom flask affixed with a Dean-Stark trap, condenser, mechanical stirrer, and nitrogen inlet (2 scfh) 3,3'-BPoDA (41.61 g, 86.98 mmol), m-PD (5.408 g, 50.01 mmol), 4,4'-DDS (10.16 g, 40.91 mmol), and sulfolane (99.4 g) were added. The flask was placed in an oil bath at 25° C. and began to heat to 240° C. oil bath with an agitation of 150-200 rpm.

After 15 minutes, the oil bath temperature reached 160° C. and a homogenous orange-yellow solution was observed. After an additional five minutes, the temperature reached 193° C. and agitation was increased to 250 rpm. After heating for a total of three hours, the oil bath temperature reached 240° C. and then phthalic anhydride (1.452 g, 9.803 mmol) was added. After an additional three hours, a sample was taken for analysis. GPC: weight average MW=27,680 grams per mole; Mn=11,951 grams per mole; PDI=2.32; Mz/Mw=1.38; IC-Extract: sulfates (13.7 ppm), chlorides (2.9 ppm), phosphates (<0.5 ppm), nitrates (<0.5 ppm), nitrites (<0.5 ppm).

Example 17

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), phthalic anhydride (0.726 g, 4.90 mmol), m-PD (2.70 g, 25.0 mmol), 4,4'-DDS (5.08 g, 20.5 mmol), and NMP (109 g) were added. The flask was placed in an oil bath at 25° C. and began to heat to 200° C. oil bath with an agitation of 150-200 rpm.

After 10 minutes, the oil bath temperature reached 125° C. and the mixture became a homogenous yellow-orange solution whereupon agitation was increased to 200 rpm. The target oil bath temperature of 200° C. was obtained within 77 minutes of heating, after which 46 g of distillate was removed from the trap to give a 30 wt % solids solution and then the nitrogen sweep was reduced to 0.5 scfh. After a total of seven hours and 35 minutes, the homogenous light orange polymer solution was poured into a foil pan and cooled to ambient temperature. A sample was devolatilized (hot block) for 20 minutes at 380-385° C. under nitrogen. ICP-Dig: sodium (16.1), potassium (12.5 ppm), zinc (47.3 ppm), calcium (24.6 ppm), aluminum (2.6 ppm), iron (16.1 ppm), titanium (2.5 ppm), phosphorus (9.2 ppm); IC-Extract: sulfates (22.2 ppm), chlorides (26.4 ppm), phosphates (<0.5 ppm), nitrates (<0.5 ppm), nitrites (<0.5 ppm).

Example 18

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), m-PD (2.70 g, 25.0 mmol), 4,4'-DDS (5.08 g, 20.5 mmol), and DMZ (109 g) were added. The flask was placed in an oil bath at 25° C. and began to heat to 200° C. oil bath with an agitation of 150-200 rpm.

After 10 minutes, the oil bath temperature reached 128° C. and the mixture became a homogenous orange solution whereupon agitation was increased to 200 rpm. The target oil bath temperature of 200° C. was obtained within 40-45 minutes of heating. After a total of 3.5 hours, 46 g of distillate was removed from the trap to give a 30 wt % solids solution and then the nitrogen sweep was reduced to 0.5 scfh. After a total of seven hours and 35 minutes, the homogenous orange polymer solution was poured into a foil pan and cooled to ambient temperature. A sample was devolatilized (hot block) for 20 minutes at 380-385° C. under nitrogen. ICP-Dig: sodium (9.9), potassium (10.1 ppm), zinc (32.8 ppm), calcium (19.4 ppm), aluminum (2.1 ppm), iron (8.5 ppm), titanium (1.7 ppm), phosphorus (8.8 ppm); IC-Extract: sulfates (12.6 ppm), chlorides (4.9 ppm), phosphates (<0.5 ppm), nitrates (<0.5 ppm), nitrites (<0.5 ppm).

Example 19

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), m-PD (2.70 g, 25.0 mmol), 4,4'-DDS (5.08 g, 20.5 mmol), and DMA (109 g) were added. The flask was placed in an oil bath at 25° C. and began to heat to 200° C. oil bath with an agitation of 150-200 rpm.

After 27 minutes, the oil bath temperature reached 112° C. and the mixture became a homogenous orange solution whereupon agitation was increased to 200 rpm. The target oil bath temperature of 200° C. was obtained within 75 minutes of heating after which 46 g of distillate was removed from the trap to give a 30 wt % solids solution and then the nitrogen sweep was reduced to 0.5 scfh. After a total of seven hours and 25 minutes the homogenous orange polymer solution was poured into a foil pan and cooled to ambient temperature. A sample was devolatilized (using a hot block) for 20 minutes at 380-385° C. under nitrogen. ICP-Dig: sodium (10), potassium (7 ppm), zinc (49 ppm), calcium (13 ppm), aluminum (4 ppm), iron (10 ppm), titanium (0 ppm), phosphorus (10 ppm); IC-Extract: sulfates (7.7 ppm), chlorides (6.1 ppm), phosphates (<0.5 ppm), nitrates (2.4 ppm), nitrites (<0.5 ppm).

Example 20

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), m-PD (2.70 g, 25.0 mmol), 4,4'-DDS (5.08 g, 20.5 mmol), and ethyl benzoate (110 g) were added. The flask was placed in an oil bath at 25° C. and began to heat to 200° C. oil bath with an agitation of 150-200 rpm.

After 40 minutes, the oil bath temperature reached 170° C. and a glue ball stage was observed. After an additional five minutes, the oil bath temperature reached 179° C. and the mixture became a homogenous orange solution whereupon agitation was increased to 200 rpm. The target oil bath temperature of 200° C. was obtained within 77 minutes of heating after which 46 g of distillate was removed from the trap to give a 30 wt % solids solution and then the nitrogen sweep was reduced to 0.5 scfh. After an additional hour of heating at 200° C., the mixture became biphasic and a dough-like polymer was observed. After a total of seven hours and 20 minutes the mixture was poured and scraped into a foil pan and cooled to ambient temperature. A sample was devolatilized (using a hot block) for 20 minutes at 380-385° C. under nitrogen. ICP-Dig: sodium (16), potassium (10 ppm), zinc (11 ppm), calcium (18 ppm), aluminum (8 ppm), iron (32 ppm), titanium (0 ppm), phosphorus (13 ppm); IC-Extract: sulfates (6.2 ppm), chlorides (1.7 ppm), phosphates (<0.5 ppm), nitrates (<0.5 ppm), nitrites (<0.5 ppm).

Example 21

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), m-PD (2.70 g, 25.0 mmol), 4,4'-DDS (5.08 g, 20.5 mmol), and diphenyl ether (109 g) were added. The flask was placed in an oil bath at 25° C. and began to heat to 200° C. oil bath with an agitation of 120 rpm.

After 50 minutes, the oil bath temperature reached 180° C. and a glue ball stage (containing a biphasic mixture with a solid mass of prepolymer) was observed. After an additional seven minutes, the oil bath temperature reached 192° C. and the reaction became a biphasic mixture whereupon agitation was increased to 200 rpm. After a total of three hours of heating, the mixture became a viscous opaque mixture and the water distillate was removed from the trap. After a total of seven hours and 35 minutes the mixture was scraped with a metal spatula into a foil pan and cooled to ambient temperature. A sample was devolatilized (using a hot block) for 20 minutes at 380-385° C. under nitrogen. ICP-Dig: sodium (8.6), potassium (8.4 ppm), zinc (28.1 ppm), calcium (18.6 ppm), aluminum (2 ppm), iron (23.4 ppm), titanium (1.7 ppm), phosphorus (11.1 ppm); IC-Extract: sulfates (3.1 ppm), chlorides (1.9 ppm), phosphates (<0.5 ppm), nitrates (<0.5 ppm), nitrites (<0.5 ppm).

Example 22

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), m-PD (2.70 g, 25.0 mmol), 4,4'-DDS (5.08 g, 20.5 mmol), and phenetole (109 g) were added. The flask was placed in an oil bath at 25° C. and began to heat to 200° C. oil bath with an agitation of 150-200 rpm.

After 25 minutes, the oil bath temperature reached 190° C. and the reaction became a biphasic mixture. After an additional three minutes, the oil bath temperature reached 195° C. After an additional twelve minutes, the mixture thinned and agitation was increased to 200 rpm. After an additional two minutes, the target oil bath temperature of 200° C. was reached and 46 g of distillate was drained from the trap to provide reaction mixture at 30 wt % solids.

After a total of three and a half hours of heating, the mixture became a viscous taffy-like viscous mixture. Heating was continued, and it was observed that the polymer solids climbed up the agitator shaft. After a total of seven hours and 45 minutes the mixture was scraped with a metal spatula into a foil pan and cooled to ambient temperature. A sample was devolatilized (using a hot block) for 20 minutes at 380-385° C. under nitrogen. ICP-Dig: sodium (16), potassium (12 ppm), zinc (13 ppm), calcium (27 ppm), aluminum (7 ppm), iron (27 ppm), titanium (0 ppm), phosphorus (16 ppm); IC-Extract: sulfates (7.7 ppm), chlorides (1.2 ppm), phosphates (<0.5 ppm), nitrates (<0.5 ppm), nitrites (<0.5 ppm).

Example 23

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), phthalic anhydride (0.726 g, 4.90 mmol), m-PD (2.70 g, 25.0 mmol), 4,4'-DDS (5.08 g, 20.5 mmol), and triglyme (108 g) were added. The flask was placed in an oil bath at 25° C. and began to heat to 200° C. oil bath with an agitation of 120 rpm.

After 35 minutes, the oil bath temperature reached 185° C. and a homogenous mixture was observed. After an additional five minutes, the agitation was increased to 200 rpm. After a total of 45 minutes of heating, the mixture became opaque and the target oil bath temperature of 200° C. was achieved. After heating for an additional hour, 46 g of distillate was removed from the trap to provide reaction mixture at 30 wt % solids. The nitrogen sweep was reduced to 0.5 scfh. After a total of seven hours and 20 minutes the mixture was poured and scraped with a metal spatula into a foil pan and cooled to ambient temperature. A sample was devolatilized (using a hot block) for 20 minutes at 380-385° C. under nitrogen. ICP-Dig: sodium (17), potassium (31 ppm), zinc (17 ppm), calcium (24 ppm), aluminum (9 ppm), iron (26 ppm), titanium (0 ppm), phosphorus (13 ppm); IC-Extract: sulfates (3.4 ppm), chlorides (0.7 ppm), phosphates (<0.5 ppm), nitrates (<0.5 ppm), nitrites (<0.5 ppm).

Comparative Example 24

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), m-PD (2.70 g, 25.0 mmol), 4,4'-DDS (5.08 g, 20.5 mmol), and o-DCB (109 g) were added. The flask was placed in an oil bath at 25° C. and began to heat to 200° C. oil bath with an agitation of 120 rpm.

After 35 minutes, the oil bath temperature reached 155° C. and a glue ball phase (containing a biphasic mixture with a solid mass of prepolymer) was observed during which agitation was reduced to 80-100 rpm. After an additional eight minutes, the oil bath temperature reached 173° C. and the mixture became a homogenous yellow solution. The agitation was then increased to 200 rpm.

After a total of 75 minutes of heating, the target oil bath temperature of 200° C. was achieved. At this point, 46 g of distillate was removed from the trap to provide reaction mixture at 30 wt % solids and the nitrogen sweep was reduced to 0.5 scfh. After a total of six hours and 45 minutes the polymerization became a viscous biphasic mixture. After an additional 70 minutes, the mixture was poured and scraped with a metal spatula into a foil pan and cooled to ambient temperature. A sample was devolatilized (using a hot block) for 20 minutes at 380-385° C. under nitrogen. ICP-Dig: sodium (16), potassium (11 ppm), zinc (7 ppm), calcium (25 ppm), aluminum (6 ppm), iron (15 ppm), titanium (0 ppm), phosphorus (12 ppm); IC-Extract: sulfates (4.6 ppm), chlorides (1.4 ppm), phosphates (<0.5 ppm), nitrates (<0.5 ppm), nitrites (<0.5 ppm).

Comparative Example 25

In a 250 mL 3-neck round bottom flask affixed with a Dean-Stark trap, condenser, mechanical stirrer, and nitrogen inlet (2 scfh) 3,3'-BPoDA (20.8 g, 43.6 mmol), PA (0.691 g, 4.67 mmol), m-PD (2.70 g, 25.0 mmol), 4,4'-DDS (5.08 g, 20.5 mmol), and DMSO (57.1 mL) were added. The flask was placed in an oil bath at 25° C. and began to heat the oil bath to 200-205° C. with an agitation of 150-200 rpm.

After 21 minutes, the oil bath temperature reached 106° C. and a homogenous yellow-orange solution was observed. After a total of 102 minutes, the target temperature was reached, and 21 g of distillate was removed from the trap to give a 40 wt % solids mixture as a viscous orange gel. Additional DMSO (20 mL) was added and the oil bath temperature was lowered to 200° C. A sample taken after 18 minutes showed a molecular weight of 4,657 grams per mole. After heating for three more hours, the mixture became a dark orange solution and the molecular weight dropped to 3,616 grams per mole.

Comparative Example 26

In a 250 mL 3-neck round bottom flask affixed with a Dean-Stark trap, condenser, mechanical stirrer, and nitrogen inlet (2 scfh) 3,3'-BPoDA (20.8 g, 43.6 mmol), PA (0.691 g, 4.67 mmol), m-PD (2.70 g, 25.0 mmol), 4,4'-DDS (5.08 g, 20.5 mmol), and formamide (55.7 mL) were added. The flask was placed in an oil bath at 25° C. and began to heat the oil bath to 170° C. with an agitation of 150-200 rpm.

After 30 minutes, the oil bath temperature reached 169° C. and a homogenous orange-yellow solution was observed. Five minutes later, the mixture became cloudy with a white precipitate. It was noted that ammonia and water were distilled overhead. After a total of two hours, a fine light-yellow slurry was observed, and GPC analysis showed decomposition products.

A variety of non-halogenated solvents were also tested to assess their performance for the condensation polymers of BPoDA with various diamines (e.g., m-PD and 4,4'-DDS) and using phthalic anhydride as a chain-terminating agent. The results are summarized in Table 4. In most cases, all reagents were added at the outset of the polymerization. Example 12 was run to determine the effect of adding the phthalic anhydride chain stopper later in the polymerization.

TABLE 4

| Example | Solvent | mol % PA | MW | PDI | Note | Tg (° C.) |
|---|---|---|---|---|---|---|
| 11 | benzonitrile | 5.25% | 29,269 | 2.16 | homogenous | 275.8 |
| 12 | benzonitrile | 5.25% | 28,005 | 2.10 | homogenous | 280.6 |
| 13 | 3-nitrotoluene | 5.25% | 28,310 | 2.15 | homogenous | 277.9 |
| 14 | p-cresol | 5.25% | 25,924 | 2.14 | homogenous | 272.5 |
| 15 | m-cresol | 5.25% | 27,572 | 2.14 | homogenous | 275.5 |
| 16 | sulfolane | 5.25% | 27,680 | 2.32 | homogenous | 253.9 |
| 17 | NMP | 5.25% | 27,046 | 2.20 | homogenous | 275.1 |
| 18 | DMZ | 5.25% | 25,751 | 2.22 | homogenous | 273.4 |
| 19 | DMA | 5.25% | 21,810 | 2.16 | homogenous | 265.2 |
| 20 | ethyl benzoate | 5.25% | 31,445 | 2.19 | biphasic | 280.5 |
| 21 | diphenyl ether | 5.25% | 32,944 | 2.05 | biphasic | 278.6 |
| 22 | phenetole | 5.25% | 30,937 | 2.10 | biphasic | 278.9 |
| 23 | triglyme | 5.25% | 30,197 | 2.54 | biphasic | 281.2 |
| 24* | o-DCB | 5.25% | 31,372 | 2.30 | biphasic | 278.5 |
| 25* | DMSO | 4.99% | ND | ND | decomposed | — |
| 26* | formamide | 4.99% | ND | ND | decomposed | — |

*Denotes comparative examples

The results showed that benzonitrile, 3-nitrotoluene, m-cresol, p-cresol, sulfolane, NMP, and DMZ solvents provided a homogenous polymerization reaction and built high molecular weight poly(etherimide). In comparison, and DMA also provided a homogenous polymerization, but the molecular weight build was somewhat subdued. Ethyl benzoate, diphenyl ether, phenetole, and triglyme solvents did obtain high molecular weight poly(etherimide) but were biphasic mixtures similar to results from a control polymerization using o-DCB as the solvent. DMSO and formamide solvents led to decomposition products. Examples 11-24 provided a poly(etherimide) with a Tg greater than 253° C. Unexpectedly, a delayed addition (2 hours) of the chain-stopper (Example 12) resulted in a marked increase in Tg (280.6° C.) versus up-front addition (Example 11) of the chain-stopper.

Examples 11-24 were devolatilized at 380-385° C. for 20 minutes to finish off the end groups. Table 5 shows that all poly(etherimide) samples had less than 25 ppm sodium and potassium, as determined by ICP-digest analysis. Also, all poly(etherimide) samples had <27 ppm of sulfates and chlorides as determined by IC-extract analysis.

TABLE 5

| Example | Solvent | Sodium (ppm) | Potassium (ppm) | Sulfates (ppm) | Chlorides (ppm) |
|---|---|---|---|---|---|
| 11 | benzonitrile | 14 | 14 | 10.7 | 3 |
| 12 | benzonitrile | 5.1 | 7.1 | 6.5 | 7.6 |
| 13 | 3-nitrotoluene | 8 | 6 | 8.8 | <0.5 |
| 14 | p-cresol | 17 | 10 | 16 | <0.5 |
| 15 | m-cresol | 20 | 13 | 7.6 | 2.8 |
| 16 | sulfolane | ND | ND | 13.7 | 2.9 |
| 17 | NMP | 24 | 19 | 22.2 | 26.4 |
| 18 | DMZ | 18 | 13 | 12.6 | 4.9 |
| 19 | DMA | 10 | 7 | 7.7 | 6.1 |
| 20 | ethyl benzoate | 16 | 10 | 6.2 | 1.7 |
| 21 | diphenyl ether | 15 | 13 | 3.1 | 1.9 |
| 22 | phenetole | 16 | 12 | 7.7 | 1.2 |
| 23 | triglyme | 17 | 31 | 3.4 | 0.7 |
| 24* | o-DCB | 16 | 11 | 4.6 | 1.4 |

*Denotes comparative example

Examples 27 and 30 used 3,3'-BPoDA which had the following profile: ICP-Dig: sodium (20 ppm), potassium (7 ppm), zinc (0 ppm), calcium (2.6 ppm), aluminum (0 ppm), iron (3 ppm), titanium (0 ppm), phosphorus (8 ppm); IC-Extract: sulfates (1.2 ppm), chloride (<0.5 ppm), phosphates (<0.5 ppm), nitrates (<0.5 ppm), nitrites (<0.5 ppm); UPLC: 3,3'-BPoDA (94.20%), BPoAnhDA (4.91%).

Examples 28 and 29 used 3,3'-BPoDA which had the following profile: ICP-Dig: sodium (5 ppm), potassium (41 ppm), zinc (2 ppm), calcium (4 ppm), aluminum (3 ppm), iron (9 ppm), titanium (0 ppm), phosphorus (10 ppm); IC-Extract: sulfates (4.6 ppm), chloride (<0.5 ppm), phosphates (<0.5 ppm), nitrates (<0.5 ppm), nitrites (<0.5 ppm); UPLC: 3,3'-BPoDA (96.26%), BPoAnhDA (3.74%).

Example 27

In a 250 mL 3-neck round bottom flask affixed with a Dean-Stark trap, condenser, mechanical stirrer, and nitrogen inlet (2 scfh) 3,3'-BPoDA (29.26 g, 61.16 mmol), PA (1.08 g, 7.30 mmol), p-PD (6.98 g, 64.5 mmol), and benzonitrile (137 g) were added. The flask was placed in an oil bath at 25° C. and began to heat to 180° C. oil bath with an agitation of 150 rpm.

After two hours, the mixture became a fine slurry and 56.4 g of distillate was removed from the trap to provide reaction mixture at 30 wt % solids. The nitrogen sweep was reduced to 0.5 scfh and heating was continued overnight. After a total of 22.5 hours, the slurry was poured into a jar and cooled to ambient temperature. A sample was devolatilized (using a hot block) for 20 minutes at 380-385° C. under nitrogen. GPC: weight average MW=14,292 grams per mole; Mn=2,763 grams per mole; PDI=5.17; Mz/Mw=18.03; ICP-Dig: sodium (10.4), potassium (<5 ppm), zinc (<1 ppm), calcium (5.0 ppm), aluminum (1.3 ppm), iron (2.7 ppm), titanium (<1 ppm), phosphorus (<10 ppm); IC-Extract: sulfates (11.3 ppm), chlorides (6.6 ppm), phosphates (<0.5 ppm), nitrates (<0.5 ppm), nitrites (<0.5 ppm).

Example 28

In a 250 mL 3-neck round bottom flask affixed with a Dean-Stark trap, condenser, mechanical stirrer, and nitrogen inlet (2 scfh) 3,3'-BPoDA (29.27 g, 61.18 mmol), PA (1.08 g, 7.30 mmol), p-PD (6.98 g, 64.6 mmol), and m-cresol (133 mL) were added. The flask was placed in an oil bath at 25° C. and began to heat to 200° C. oil bath with an agitation of 150-200 rpm.

After 17 minutes, the oil bath temperature reached 103° C. and a glue ball stage was observed. After an additional five minutes, the agitation was increased to 300 rpm. After a total of 40 minutes, the oil bath temperature reached 172° C. and a homogenous clear orange solution was obtained. After a total of one hour, a thick yellow slurry was observed then additional m-cresol (50 mL) was added and the solids were broken up with a metal spatula. After an additional 90 minutes, the yellow slurry was transferred to a 500 mL 3-neck round bottom flask with Dean-Stark trap, condenser, mechanical stirrer, and nitrogen inlet. The transfer was complete with additional m-cresol (150 mL). Heating of the 9 wt % solids yellow slurry was continued in the 200° C. oil bath. After a total heating time of six hours, agitation of the viscous slurry was increased to 520 rpm. After an additional 90 minutes the mixture was filtered onto a medium-fritted glass funnel to collect the polymer solids. A sample was devolatilized (using a hot block) for 20 minutes at 380-385° C. under nitrogen. GPC: weight average Mw=10,722 grams per mole; Mn=4,813 grams per mole; PDI=2.23; Mz/Mw=1.59.

Example 29

In a 250 mL 3-neck round bottom flask affixed with a Dean-Stark trap, condenser, mechanical stirrer, and nitrogen inlet (2 scfh) 3,3'-BPoDA (20.81 g, 43.49 mmol), PA (0.726 g, 4.90 mmol), p-PD (3.69 g, 34.1 mmol), 4,4'-ODA (2.28 g, 11.4 mmol), and benzonitrile (102 g) were added. The flask was placed in an oil bath at 25° C. and began to heat to 200° C. oil bath with an agitation of 120 rpm.

After 12 minutes, the oil bath temperature reached 111° C. and a suspension was observed. After an additional 13 minutes, a glue ball stage was observed between 148-152° C. (oil bath temperature). The mixture became a homogenous orange solution and then agitation was increased to 200 rpm. After a total of one hour and 50 minutes of heating, the target oil bath temperature of 200° C. was achieved and the mixture became an opaque yellow slurry. At this point, 46 g of distillate was removed from the trap to provide reaction mixture at 30 wt % solids and then the nitrogen sweep was reduced to 0.5 scfh. After a total of seven hours and 35 minutes the yellow slurry was poured into a foil pan and cooled to ambient temperature. A sample was devolatilized (hot block) for 20 minutes at 380-385° C. under nitrogen. GPC: weight average Mw=24,030 grams per mole; Mn=9,873 grams per mole; PDI=2.43; Mz/Mw=1.54. ICP-Dig: sodium (11), potassium (7 ppm), zinc (17 ppm), calcium (12 ppm), aluminum (2 ppm), iron (7 ppm), titanium (0 ppm), phosphorus (8 ppm); IC-Extract: sulfates (4.1 ppm), chlorides (<0.5 ppm), phosphates (<0.5 ppm), nitrates (2.6 ppm), nitrites (<0.5 ppm). DSC (Tg)=280.7° C.

Example 30

In a 250 mL 3-neck round bottom flask affixed with a Dean-Stark trap, condenser, mechanical stirrer, and nitrogen inlet (2 scfh) 3,3'-BPoDA (60.02 g, 125.5 mmol), PA (2.30 g, 15.5 mmol), p-PD (10.92 g, 101.0 mmol), 4,4'-ODA (6.66 g, 33.3 mmol), and m-cresol (214.6 g) were added. The flask was placed in an oil bath at 25° C. and began to heat to 180° C. oil bath with an agitation of 120 rpm.

After 45 minutes, the oil bath temperature reached 112° C. and the reaction mixture solidified. Additional m-cresol (70 g) was added. After an additional 25 minutes, target oil bath temperature of 180° C. was achieved and the mixture was observed to be a homogenous gel. Additional m-cresol (60 g) was added and the oil bath temperature was adjusted to 210° C. After heating for an additional hour, 80 g of distillate was removed from the trap and then the nitrogen sweep was reduced to 0.5 scfh. After a total of seven hours and 30 minutes the homogenous gel was poured and scraped with a metal spatula into a foil pan and cooled to ambient temperature. A sample was devolatilized (using a hot block) for 20 minutes at 380-385° C. under nitrogen. GPC: weight average Mw=23,792 grams per mole; Mn=10,253 grams per mole; PDI=2.32; Mz/Mw=1.65; ICP-Dig: sodium (10.2), potassium (9.6 ppm), zinc (3.2 ppm), calcium (13.1 ppm), aluminum (1.3 ppm), iron (10.1 ppm), titanium (1.5 ppm), phosphorus (11.5 ppm); IC-Extract: sulfates (2.4 ppm), chlorides (0.9 ppm), phosphates (<0.5 ppm), nitrates (<0.5 ppm), nitrites (<0.5 ppm); DSC (Tg)=275.4° C.

Four examples were run to show that not all poly(etherimide) polymerizations run in the preferred solvents (benzonitrile and m-cresol) remain homogenous (Table 7). Under similar polymerization conditions, certain rigid poly(etherimides) will become insoluble resulting in a biphasic polymerization mixture. Unlike the polymerizations of 3,3'-BPoDA with m-PD and 4,4'-DDS which remain homogenous, the poly(etherimide) formed from 3,3'-BPoDA and p-PD (examples 27 and 28) became insoluble in both benzonitrile and m-cresol. Additionally, polymerizations of 3,3'-BPoDA with p-PD and 4,4'-ODA (example 29) also resulted in a biphasic mixture when using benzonitrile but remained homogenous in m-cresol (example 30). This highlights the non-obviousness of using these and similar solvents to prepare poly(etherimides) with the intent of maintaining a homogenous polymer solution which can then be directly devolatilized with an extruder.

total of one hour and 40 minutes, the distillate (46 g) was drained from the trap to prove a reaction mixture at 30 wt % solids. The nitrogen sweep was reduced to 0.5 scfh and after an additional six hours a sample was devolatilized (using a hot block) for 20 minutes at 380-385° C. under nitrogen. GPC: weight average Mw=27,238 grams per mole; Mn=12, 829 grams per mole; PDI=2.12; Mz/Mw=1.38. ICP-Dig: sodium (8.5), potassium (<5.0 ppm), zinc (14.6 ppm), calcium (9.9 ppm), aluminum (3.0 ppm), iron (7.3 ppm), titanium (<1.0 ppm), phosphorus (<10 ppm); IC-Extract: sulfates (18.1 ppm), chlorides (16.8 ppm), phosphates (<0.5 ppm), nitrates (<0.5 ppm), nitrites (<0.5 ppm); DSC (Tg) =272.7° C.

Example 32

In a 250 mL 3-neck round bottom flask affixed with a Dean-Stark trap, condenser, mechanical stirrer, and nitrogen inlet (2 scfh) 3,3'-BPoDA (20.806 g, 43.49 mmol), PA (0.726 g, 4.90 mmol), m-PD (2.704 g, 25.00 mmol), 4,4'-DDS (5.079 g, 20.46 mmol), m-cresol (91 g), and toluene (18.2 g) were added. The flask was placed in an oil bath at 25° C. and began to heat to 200° C. oil bath with an agitation of 150-200 rpm.

After ten minutes, the oil bath temperature reached 114° C. and a homogenous yellow-orange solution was observed, whereupon agitation was increased to 250 rpm. After a total of 55 minutes, 48 g of distillate was removed from the trap to provide reaction mixture at 30 wt % solids. The nitrogen sweep was reduced to 0.5 scfh. After a total of 7.5 hours, the solution appeared yellow in color and a sample was taken and devolatilized (using a hot block) for 20 minutes at 380-385° C. under nitrogen. GPC: weight average Mw=17, 625 grams per mole; Mn=6,987 grams per mole; PDI=2.52; Mz/Mw=1.48. DSC (Tg)=258.3° C.

TABLE 7

| Example | Solvent | mol % 3,3'-BPoDA | mol % PA | mol % p-PD | mol % 4,4'-ODA | Result | MW | Tg (° C.) |
|---|---|---|---|---|---|---|---|---|
| 27 | benzonitrile | 45.98% | 5.49% | 48.53% | 0% | slurry | 14,292 | — |
| 28 | m-cresol | 45.96% | 5.49% | 48.54% | 0% | biphasic mixture | 10,722 | — |
| 29 | benzonitrile | 46.34% | 5.22% | 36.33% | 12.11% | slurry | 24,030 | 280.7 |
| 30 | m-cresol | 45.58% | 5.64% | 36.69% | 12.08% | Homogenous viscous gel | 23,792 | 275.4 |

The following examples 31 and 32 used 3,3'-BPoDA which had the following profile: ICP-Dig: sodium (5 ppm), potassium (41 ppm), zinc (2 ppm), calcium (4 ppm), aluminum (3 ppm), iron (9 ppm), titanium (0 ppm), phosphorus (10 ppm); IC-Extract: sulfates (4.6 ppm), chloride (<0.5 ppm), phosphates (<0.5 ppm), nitrates (<0.5 ppm), nitrites (<0.5 ppm); UPLC: 3,3'-BPoDA (96.26%), BPoAnhDA (3.74%).

Example 31

In a 250 mL 3-neck round bottom flask affixed with a Dean-Stark trap, condenser, mechanical stirrer, and nitrogen inlet (2 scfh) 3,3'-BPoDA (20.806 g, 43.49 mmol), PA (0.726 g, 4.90 mmol), m-PD (2.704 g, 25.00 mmol), 4,4'-DDS (5.079 g, 20.45 mmol), benzonitrile (92 g), and toluene (18.2 g) were added. The flask was placed in an oil bath at 25° C. and began to heat to 200° C. oil bath with an agitation of 200 rpm.

After 37 minutes, the oil bath temperature reached 145° C. and a homogenous yellow solution was observed. After a The remaining polymer solution was heated overnight. After a total of 24 hours, a sample was devolatilized (using a hot block) for 20 minutes at 380-385° C. under nitrogen. GPC: weight average Mw=13,671 grams per mole; Mn=5, 033; PDI=2.72; Mz/Mw=1.56. ICP-Dig: sodium (14.8), potassium (7.1 ppm), zinc (1.7 ppm), calcium (9.6 ppm), aluminum (9.6 ppm), iron (7.8 ppm), titanium (<0.5 ppm), phosphorus (7.9 ppm); IC-Extract: sulfates (14.4 ppm), chlorides (11.7 ppm), phosphates (<0.5 ppm), nitrates (<0.5 ppm), nitrites (<0.5 ppm); DSC (Tg)=252.3° C.

Two examples were run with a dual solvent system to prepare a poly(etherimide) from 3,3'-BPoDA, m-PD, and 4,4'-DDS (Table 8). In these examples, a lower boiling solvent, toluene, was used with benzonitrile (example 31) and m-cresol (example 32) to help remove water from the system as the condensation polymerization progressed. The resulting poly(etherimide) polymers achieved high Tg values (>250° C.) as did examples without the toluene additive (Examples 11 and 15).

TABLE 8

| Example | Solvent | mol % PA | MW | PDI | Tg (° C.) |
|---|---|---|---|---|---|
| 31 | benzonitrile/toluene (5:1, m/m) | 5.25% | 27,238 | 2.12 | 272.7 |
| 32 | m-cresol/toluene (5:1, m/m) | 5.25% | 17,625 | 2.52 | 258.3 |
| 11 | benzonitrile | 5.25% | 29,269 | 2.16 | 275.8 |
| 15 | m-cresol | 5.25% | 23,712 | 2.32 | 266.0 |

Comparative Example 33

The following example used 3,3'-BPoTA which had the following profile: ICP-Dig: sodium (138 ppm), potassium (9 ppm), zinc (2 ppm), calcium (6 ppm), aluminum (2 ppm), iron (20 ppm), titanium (0 ppm), phosphorus (7 ppm), chromium (10 ppm), magnesium (19 ppm), nickel (2 ppm); IC-Extract: sulfates (301 ppm), chloride (919 ppm), phosphates (<20 ppm); UPLC: 3,3'-BPoTA and isomers (98.50%).

In a 1000 mL 3-neck round bottom flask affixed with a Dean-Stark trap, condenser, mechanical stirrer, and nitrogen inlet (2 scfh) 3,3'-BPoTA (64.48 g, 125.42 mmol), PA (1.991 g, 13.44 mmol), m-PD (7.812 g, 72.24 mmol), 4,4'-DDS (14.791 g, 59.57 mmol) and benzonitrile (235 g) were added. The flask was placed in an oil bath at 25° C. and began to heat to 200° C. oil bath with an agitation of 170-200 rpm.

After approximately thirty-five minutes, the oil bath temperature reached 200° C. and a homogenous light amber solution was observed, whereupon agitation was increased to 225-250 rpm. After a total of 65 minutes, 51 g of distillate was removed from the trap to provide reaction mixture at 30 wt % solids. The nitrogen sweep was reduced to 0.5 scfh. After a total of 14 hours, the solution stayed light amber in color and a sample was taken and devolatilized (using a hot block) for 20 minutes at 380-385° C. under nitrogen. GPC: weight average Mw=8,075 grams per mole; Mn=3,379 grams per mole; PDI=2.31; Mz/Mw=1.54, DSC (Tg) =178.6° C. ICP-Dig: sodium (116), potassium (10.9 ppm), zinc (2.2 ppm), calcium (6.1 ppm), aluminum (3.8 ppm), iron (11.4 ppm), titanium (<1.0 ppm), phosphorus (<10 ppm); IC-Extract: sulfates (73.3 ppm), chlorides (3.5 ppm), phosphates (<0.5 ppm), nitrates (<0.5 ppm), nitrites (<0.5 ppm).

Comparative Example 34

The following example used 3,3'-BPoTA which had the following profile: ICP-Dig: sodium (52 ppm), potassium (10 ppm), zinc (1 ppm), calcium (1.3 ppm), aluminum (1.6 ppm), iron (0 ppm), titanium (0 ppm), phosphorus (8 ppm); IC-Total: sulfates (1031 ppm), chloride (579 ppm), fluorides (<20 ppm), bromides (<20 ppm), phosphates (<20 ppm), nitrates (224 ppm), nitrites (117 ppm); UPLC: 3,3'-BPoTA and isomers (95.47%), 4,4'-biphenol (4.53%).

In a 1000 mL 3-neck round bottom flask affixed with a Dean-Stark trap, condenser, mechanical stirrer, and nitrogen inlet (2 scfh) 3,3'-BPoDA (64.51 g, 125.42 mmol), PA (1.993 g, 13.44 mmol), m-PD (7.814 g, 72.24 mmol), 4,4'-DDS (14.798 g, 59.57 mmol) and benzonitrile (235 g) were added. The flask was placed in an oil bath at 25° C. and began to heat to 200° C. oil bath with an agitation of 170-200 rpm.

After about forty minutes, the oil bath temperature reached 200° C. and a homogenous dark amber colored solution was observed, whereupon agitation was increased to 225-250 rpm. After a total of 50 minutes, 49 g of distillate was removed from the trap to provide reaction mixture at 30 wt % solids. The nitrogen sweep was reduced to 0.5 scfh. After a total of 16 hours, the solution stayed dark amber in color and a sample was taken and devolatilized (using a hot block) for 20 minutes at 380-385° C. under nitrogen. GPC: weight average Mw=25,851 grams per mole; Mn=11,214 grams per mole; PDI=2.30; Mz/Mw=1.42, DSC (Tg) =200.9° C. ICP-Dig: sodium (85.9), potassium (10.2 ppm), zinc (2.9 ppm), calcium (16.5 ppm), aluminum (6.7 ppm), iron (12.7 ppm), titanium (<1 ppm), phosphorus (<10 ppm); IC-Extract: sulfates (5.5 ppm), chlorides (<0.5 ppm), phosphates (<0.5 ppm), nitrates (<0.5 ppm), nitrites (<0.5 ppm).

Comparative Example 35

The following example used 3,3'-BPoDA which had the following profile: ICP-Dig: sodium (7 ppm), potassium (22 ppm), zinc (2 ppm), calcium (6 ppm), aluminum (4 ppm), iron (15 ppm), titanium (1 ppm), phosphorus (11 ppm); IC-Extract: sulfates (8.2 ppm), chloride (<0.5 ppm), phosphates (<0.5 ppm), nitrates (<0.5 ppm), nitrites (<0.5 ppm); UPLC: 3,3'-BPoDA 91.75%), BPoAnhDA (6.78%).

This example also used m-PD which had the following profile: ICP-Dig: sodium (485 ppm), potassium (13 ppm), zinc (1 ppm), calcium (11 ppm), aluminum (0 ppm), iron (0 ppm), titanium (0 ppm), phosphorus (8 ppm); IC-Extract: sulfates (<0.5 ppm), chloride (153.8 ppm), phosphates (<0.5 ppm), nitrates (<0.5 ppm), nitrites (<0.5 ppm).

In a 250 mL 3-neck round bottom flask affixed with a Dean-Stark trap, condenser, mechanical stirrer, and nitrogen inlet (2 scfh) 3,3'-BPoDA (20.59 g, 43.0 mmol), PA (0.762 g, 5.14 mmol), m-PD (2.70 g, 25.0 mmol), 4,4'-DDS (5.08 g, 100 mass %, 20.5 mmol), and benzonitrile (63 mL) were added. The flask was placed in an oil bath at 25° C. and began to heat the oil bath to 205° C. with an agitation of 150-200 rpm.

After 20 minutes, the oil bath temperature reached 176° C. and a homogenous orange-yellow solution was observed. After a total of 65 minutes, the target temperature was reached, and 22.5 g of distillate was removed from the trap to give a 40 wt % solids solution. The nitrogen sweep was reduced to 0.5 scfh and after 23 hours at 200-205° C. the polymer solution was poured into a foil pan then cooled to ambient temperature. A sample was devolatilized (using a hot block) for 20 minutes at 380° C. under nitrogen. GPC: weight average Mw=29,037 grams per mole; Mn=12,818 grams per mole; PDI=2.27; Mz/Mw=1.50. ICP-Dig: sodium (171), potassium (9 ppm), zinc (34 ppm), calcium (12 ppm), aluminum (3 ppm), iron (4 ppm), titanium (0 ppm), phosphorus (57 ppm); IC-Extract: sulfates (63.5 ppm), chlorides (12.2 ppm), phosphates (5.4 ppm), nitrates (2.5 ppm), nitrites (3.5 ppm); DSC (Tg): 275.8° C.

Table 9 shows some comparative examples of poly(etherimides) formed from the polycondensation of 3,3'-BPoDA with m-PD and 4,4'-DDS in the presence of phthalic anhydride as a chain stopper. The 3,3'-BPoTA used in example 33 had high levels of metals and anions which resulted in a poly(etherimide) with low molecular weight, low Tg (178.6° C.), and high sodium content. Examples 34 and 35 involved cyclization of 3,3'-BPoTA to 3,3'-BPoDA which consequently reacted with the diamines (in situ) in benzonitrile to obtain the resulting poly(etherimides). The 3,3'-BPoTA used in example 34 also had high levels of sodium and anions in combination with elevated levels of 4,4'-biphenol (an organic contaminant). This material produced a poly(etherimide) of higher molecular weight, but with a low Tg (200.9° C.) and high sodium content. Example 35 used a diamine precursor with high sodium levels. This produced a poly(etherimide) with high molecular weight, high Tg (275.8°), but also high sodium content (171 ppm). All comparative examples 33-35 showed elevated levels of inorganic contaminants and the polymer films obtained after hot-pressing at 380-385° C. were brittle and darker in color. This will adversely affect the transparency and heat-stability needed for the end-use application. Further, the results show that the resulting polymer properties were not comparable to that of polymers obtained via procedures used in the inventive examples.

TABLE 9

| Example | Solvent | mol % PA | MW | PDI | Tg (° C.) | Sodium (ppm) | Sulfates (ppm) | Chlorides (ppm) |
|---|---|---|---|---|---|---|---|---|
| 33* | Benzonitrile | 5.0% | 8,075 | 2.31 | 178.6 | 116 | 73.3 | 2.5 |
| 34* | Benzonitrile | 5.0% | 25,851 | 2.30 | 200.9 | 85.9 | 5.5 | <0.5 |
| 35* | Benzonitrile | 5.5% | 29,037 | 2.27 | 275.8 | 171 | 63.5 | 12.2 |

*Denotes comparative example

The transmission of films prepared from several inventive poly(etherimide) examples with comparative poly(etherimides) are shown below in table 10. These examples were injection molded into optical plaques with dimensions of 50 mm×75 mm×1 mm, using 380° C. to 400° C. for melt temperature and 150° C. to 200° C. for mold temperature. The term "percent light transmission" or "% T" refers to the ratio of transmitted light to incident light, and can be measured according to ASTM D 1003-07. These measurements can be taken on the molded articles between 0.1 mm and 0.3 mm thick films prepared on a hot press at 380° C. to 400° C. Polymer film examples 11, 15, 16, and 18 were prepared from non-halogenated solvents and contained 20 ppm or less of sodium. Each had similar or better transmission than films prepared from o-DCB (example 24) at both visible (630 nm) and infrared (850, 1310, 1550 nm) wavelengths. In contrast, example 35 was a poly(etherimide) film prepared from benzonitrile and contained high amounts of sodium (171 ppm). This example had significantly reduced transmission in all wavelengths tested.

TABLE 10

| Example | solvent | Sodium (ppm) | Thickness (mm) | % T (630 nm) | % T (850 nm) | % T (1310 nm) | % T (1550 nm) |
|---|---|---|---|---|---|---|---|
| 11 | PhCN | 14 | 0.18 | 81.2 | 83.1 | 82.0 | 82.6 |
| 15 | m-cresol | 20 | 0.16 | 79.8 | 83.4 | 83.9 | 84.2 |
| 16 | sulfolane | ND | 0.16 | 84.6 | 81.6 | 85.7 | 85.9 |
| 18 | DMZ | 18 | 0.12 | 82.4 | 83.2 | 83.1 | 83.9 |
| 24* | o-DCB | 16 | 0.22 | 80 | 81.5 | 81.5 | 80.4 |
| 35* | PhCN | 171 | 0.16 | 60.5 | 62.1 | 62.3 | 62.4 |

*Denotes comparative example

Comparative Example 36

To a 250 mL 3-neck round-bottom flask with mechanical stirrer, Dean-Stark trap and condenser, 3,3'-BPoTA (15 g, 29.2 mmol) and cyclohexanone (58.5 mL) was added to make a 20 wt % mixture. The flask was then placed in an oil bath at 160° C. under nitrogen. Fresh cyclohexanone was added to the reaction flask to make up the solvent loss in the Dean-Stark trap. Samples were taken every hour from the heterogeneous yellow solution to monitor the progress of the reaction by UPLC analysis. Occasionally, solids were scraped from the agitator blade and shaft with a metal spatula. After 8 hours, UPLC analysis indicated the reaction was essentially complete. The mixture was then cooled to 50° C. to form a light off-white precipitate in cyclohexanone. The product was collected by filtration onto a medium-fritted glass funnel and then washed with methanol (125 mL). The product was allowed to dry in the vacuum oven at 140-145° C. until a consistent mass was obtained. In this manner, 10.57 g of the 3,3'-BPoDA product was collected.

Example 37

To a 250 mL 3-neck round-bottom flask with mechanical stirrer, Dean-Stark trap and condenser, 3,3'-BPoTA (15 g, 29.2 mmol) and m-cresol (53.7 mL) was added to make a 20 wt % mixture. The flask was then placed in an oil bath at 160° C. under nitrogen. Fresh m-cresol was added to the reaction flask to make up the solvent loss in the Dean-Stark trap. Samples were taken every hour from the homogenous yellow solution to monitor the progress of the reaction by UPLC analysis. After 3 hours, UPLC analysis indicated the reaction was complete. The mixture was then cooled to 50° C. to form a light off-white precipitate in m-cresol. The product was collected by filtration onto a medium-fritted glass funnel and then washed with methanol (125 mL). The product was allowed to dry in the vacuum oven at 140-145° C. until a consistent mass was obtained. In this manner, 13.09 g of the 3,3'-BPoDA product was collected.

Example 38

To a 250 mL 3-neck round-bottom flask with mechanical stirrer, Dean-Stark trap and condenser, 3,3'-BPoTA (15 g, 29.2 mmol) and m-cresol (53.7 mL) was added to make a 20 wt % mixture. The flask was then placed in an oil bath at 210° C. under nitrogen. Fresh m-cresol was added to the reaction flask to make up the solvent loss in the Dean-Stark trap. Samples were taken every half hour from the homogenous yellow solution to monitor the progress of the reaction by UPLC analysis. After 0.5-1 hour, UPLC analysis indicated the reaction was complete. The mixture was then cooled to 50° C. to form a light off-white precipitate in m-cresol. The product was collected by filtration onto a fine-fritted glass funnel and then washed with methanol (50° C., 3×20 mL) and then DI water (60-70° C., 2×20 mL). The product was allowed to dry in the vacuum oven at 140-145° C. until a consistent mass was obtained. In this manner, the 3,3'-BPoDA product was collected as a white solid.

Example 39

To a 250 mL 3-neck round-bottom flask with mechanical stirrer, Dean-Stark trap and condenser, 3,3'-BPoTA (15 g, 29.2 mmol) and sulfolane (44 mL) was added to make a 20 wt % mixture. The flask was then placed in an oil bath at 220° C. under nitrogen. Fresh sulfolane was added to the reaction flask to make up the solvent loss in the Dean-Stark trap. Samples were taken from the homogeneous yellow solution every half hour to monitor the progress of the reaction by UPLC analysis. After 0.5-1 hour, UPLC analysis indicated the reaction was complete. The mixture was then cooled to 50° C. to form a light off-white precipitate in sulfolane. The product was collected by filtration onto a medium-fritted glass funnel and then washed with methanol (125 mL). The product was allowed to dry in the vacuum oven at 140-145° C. until a consistent mass was obtained. In this manner, 15.06 g of the 3,3'-BPoDA product was collected as a white solid.

Table 11 below shows a comparison of ring-closure in cyclohexanone, m-cresol, and sulfolane at various temperatures. Comparative example 36 required eight hours to completion at 160° C. (oil bath temperature, solvent boiling point=155.65° C.) and remained heterogeneous throughout the reaction. Examples 37 and 38 show that m-cresol was superior to cyclohexanone because cycle times were reduced to three hours (at 160° C.) and 0.5-1 hour (at 210° C.). Because m-cresol is a polar aprotic solvent with a higher boiling point (202.8° C.) than cyclohexanone, the reactions remained homogenous. In a similar fashion, example 39 in sulfolane required only 0.5-1 hour to completion at 220° C. (oil bath temperature, solvent boiling point=285° C.). Additionally, both m-cresol and sulfolane provided higher conversion (96.4-96.9%) compared to cyclohexanone (93.0%) because fewer impurities were observed in their reaction mixtures.

TABLE 11

| Example | Solvent | Temperature (° C.) | Cycle Time (hours) | Observation | % Product |
|---|---|---|---|---|---|
| 36* | cyclohexanone | 160 | 8 | heterogeneous | 93.0% |
| 37 | m-cresol | 160 | 3 | homogenous | 96.4% |
| 38 | m-cresol | 210 | 0.5-1 | homogenous | 96.8% |
| 39 | sulfolane | 220 | 0.5-1 | homogenous | 96.9% |

*Denotes comparative example

This disclosure further encompasses the following aspects.

Aspect 1: A method of making a biphenol dianhydride composition, the method comprising: heating a first solution comprising a biphenol tetraacid of the formula

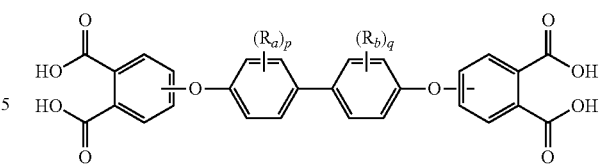

wherein $R^a$ and $R^b$ are each independently a halogen or a monovalent $C_{1-6}$ alkyl group and p and q are each independently an integer of 0 to 4, preferably wherein p and q are each 0; at least one ionic species comprising sodium ions, potassium ions, calcium ions, zinc ions, aluminum ions, titanium ions, phosphorus ions, iron ions, phosphate ions, sulfate ions, chloride ions, nitrate ions, nitrite ions, and sulfite ions; and a non-halogenated solvent comprising ethyl benzoate, diphenyl ether, phenetole, triglyme, benzonitrile, sulfolane, m-cresol, o-cresol, p-cresol, 1-nitrotoluene, 2-nitrotoluene, 3-nitrotoluene, 4-nitrotoluene, N-methyl-pyrrolidinone, 1,3-dimethyl-2-imidazolidinone, sulfolane, dimethyl acetamide, or a combination thereof; under conditions effective to provide a second solution comprising a corresponding biphenol dianhydride, and at least one of sodium ions, potassium ions, calcium ions, zinc ions, aluminum ions, titanium ions, phosphorus ions, iron ions, phosphate ions, sulfate ions, chloride ions, nitrate ions, and nitrite ions, and the solvent.

Aspect 2: The method of claim 1, further comprising cooling the second solution to a temperature effective to precipitate the biphenol dianhydride; isolating the biphenol dianhydride from the second solution; and optionally washing the isolated biphenol dianhydride with an organic solvent, water, or a combination thereof.

Aspect 3: The method of aspect 2, further comprising filtering the second solution prior to cooling the second solution to remove ionic species or filtering the second solution prior to polymerization to remove ionic species.

Aspect 4: A method for the purification of a biphenol dianhydride, the method comprising: removing an ionic species from a solution comprising a biphenol dianhydride and a non-halogenated solvent, the non-halogenated solvent comprising ethyl benzoate, diphenyl ether, phenetole, triglyme, benzonitrile, sulfolane, m-cresol, o-cresol, p-cresol, 1-nitrotoluene, 2-nitrotoluene, 3-nitrotoluene, 4-nitrotoluene, N-methyl-pyrrolidinone, 1,3-dimethyl-2-imidazolidinone, sulfolane, dimethyl acetamide, or a combination thereof, the method comprising: adsorbing the ionic species from the solution by an adsorbent comprising celite, diatomaceous earth, silica, alumina, or a combination thereof; crystallizing the biphenol dianhydride from the solution; filtering the solution to remove the ionic species; or a combination thereof.

Aspect 5: The method of any of aspects 1 to 4, wherein the biphenol dianhydride is an isomer mixture, preferably wherein 10-100 weight percent of the biphenol dianhydride have the divalent bonds of the biphenol group of the biphenol dianhydride are in the 3,3' position, more preferably wherein 90-100 weight percent of the biphenol dianhydride have the divalent bonds of the biphenol group of the biphenol dianhydride are in the 3,3' position.

Aspect 6: The method of any of aspects 1 to 5, wherein the purified biphenol dianhydride comprises less than 25 ppm each of sodium ions, potassium ions, calcium ions, zinc ions, aluminum ions, titanium ions, phosphorus ions, and iron ions; less than 110 ppm total of sodium ions, potassium ions, calcium ions, zinc ions, aluminum ions, titanium ions, phosphorus ions, and iron ions; less than 20 ppm each of phosphate ions, sulfate ions, sulfite ions chloride ions, nitrate ions, and nitrite ions, preferably less than 45 ppm each of $NaHSO_3$, $Na_2SO_4$, $KHSO_3$, $K_2SO_4$, $NaNO_3$, $NaNO_2$, $KNO_3$, $KNO_2$, NaCl, KCl, $CaSO_4$, $Ca(NO_3)_2$; and less than 50 ppm total of phosphate ions, sulfate ions, chloride ions, nitrate ions, and nitrite ions.

Aspect 7: A biphenol dianhydride made by the method of any one or more of aspects 1 to 6.

Aspect 8: A poly(etherimide) derived from the biphenol dianhydride of aspect 7 and an organic diamine, preferably wherein the organic diamine is 4,4'-diaminodiphenylsulfone, 3,4'-diaminodiphenylsulfone, 3,3'-diaminodiphenylsulfone, meta-phenylene diamine, para-phenylene diamine, ortho-phenylene diamine, 4,4'-oxydianiline, 3,3'-oxydianiline, 3,4'-oxydianiline, or a combination thereof.

Aspect 9: The poly(etherimide) of aspect 8, wherein the poly(etherimide) comprises less than 25 ppm each of sodium ions, potassium ions, calcium ions, zinc ions, aluminum ions, titanium ions, phosphorus ions, and iron ions and less than 20 ppm each of phosphate ions, sulfate ions, sulfite ions, chloride ions, nitrate ions, and nitrite ions.

Aspect 10: A method of making the poly(etherimide) of any of aspects 8 to 9, the method comprising: contacting the biphenol dianhydride with the organic diamine in the presence of an aromatic non-halogenated solvent under conditions effective to provide the poly(etherimide).

Aspect 11: The method of aspect 10, wherein the aromatic non-halogenated solvent comprises benzonitrile, 1-nitrotoluene, 2-nitrotoluene, 3-nitrotoluene, 4-nitrotoluene, m-cresol, o-cresol, p-cresol, N-methyl-pyrrolidinone, sulfolane, triglyme, phenetole, ethyl benzoate, dimethyl acetamide, diphenyl ether, and 1,3-dimethyl-2-imidazolidinone, or a combination thereof.

Aspect 12: The method of aspect 10 or 11, further comprising devolatilization of the poly(etherimide).

Aspect 13: An article comprising the poly(etherimide) of any one of aspects 8 to 9.

Aspect 14: The poly(etherimide) of aspects 8 to 9, wherein an article molded from the poly(etherimide) or a pressed film comprising the poly(etherimide) has a percent transmission that is 65% at 630 nanometers, 850 nanometers, 1310 nanometers, and 1550 nanometers, measured according to ASTM D 1003-07 at 0.16 mm thickness.

Aspect 15: The article of aspect 14, wherein the article is an optical component, preferably a lens.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. The term "combination thereof" as used herein includes one or more of the listed elements, and is open, allowing the presence of one or more like elements not named. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl ($—HC=CH_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene ($—CH_2—$) or, propylene ($—(CH_2)_3—$)). "Cycloalkylene" means a divalent cyclic alkylene group, $—C_nH_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group.

"Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a $C_{1-9}$ alkoxy, a $C_{1-9}$ haloalkoxy, a nitro (—$NO_2$), a cyano (—CN), a $C_{1-6}$ alkyl sulfonyl (—$S(=O)_2$-alkyl), a $C_{6-12}$ aryl sulfonyl (—$S(=O)_2$-aryl), a thiol (—SH), a thiocyano (—SCN), a tosyl ($CH_3C_6H_4SO_2$—), a $C_{3-12}$ cycloalkyl, a $C_{2-12}$ alkenyl, a $C_5I_2$ cycloalkenyl, a $C_{6-12}$ aryl, a $C_{7-13}$ arylalkylene, a $C_{412}$ heterocycloalkyl, and a $C_{3-12}$ heteroaryl instead of hydrogen, provided that the substituted atom's normal valence is not exceeded. The number of carbon atoms indicated in a group is exclusive of any substituents. For example —$CH_2CH_2CN$ is a $C_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of making a biphenol dianhydride composition, the method comprising:
heating a first solution comprising
a biphenol tetraacid of the formula

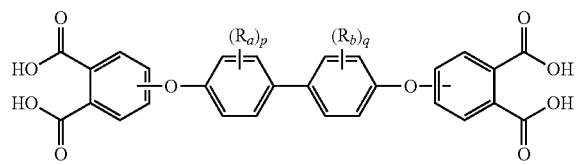

wherein $R^a$ and $R^b$ are each independently a halogen or a monovalent $C_{1-6}$ alkyl group and p and q are each independently an integer of 0 to 4;
at least one ionic species comprising sodium ions, potassium ions, calcium ions, zinc ions, aluminum ions, titanium ions, phosphorus ions, iron ions, phosphate ions, sulfate ions, chloride ions, nitrate ions, nitrite ions, and sulfite ions; and
a non-halogenated solvent comprising ethyl benzoate, diphenyl ether, phenetole, triglyme, benzonitrile, sulfolane, m-cresol, o-cresol, p-cresol, 1-nitrotoluene, 2-nitrotoluene, 3-nitrotoluene, 4-nitrotoluene,/V-methyl-pyrrolidinone, 1,3-dimethyl-2-imidazolidinone, dimethyl acetamide, or a combination thereof;
under conditions effective to provide a second solution comprising a corresponding biphenol dianhydride, the at least one of sodium ions, potassium ions, calcium ions, zinc ions, aluminum ions, titanium ions, phosphorus ions, iron ions, phosphate ions, sulfate ions, chloride ions, nitrate ions, and nitrite ions, and the solvent.

2. The method of claim 1, further comprising
cooling the second solution to a temperature effective to precipitate the biphenol dianhydride;
isolating the biphenol dianhydride from the second solution; and optionally
washing the isolated biphenol dianhydride with an organic solvent, water, or a combination thereof.

3. The method of claim 2, further comprising filtering the second solution prior to cooling the second solution to remove ionic species or filtering the second solution prior to polymerization to remove ionic species.

4. A method for the purification of a biphenol dianhydride, the method comprising:
removing an ionic species from a solution comprising a biphenol dianhydride and a non-halogenated solvent, the non-halogenated solvent comprising ethyl benzoate, diphenyl ether, phenetole, triglyme, benzonitrile, sulfolane, m-cresol, o-cresol, p-cresol, 1-nitrotoluene, 2-nitrotoluene, 3-nitrotoluene, 4-nitrotoluene, /V-methyl-pyrrolidinone, 1,3-dimethyl-2-imidazolidinone, dimethyl acetamide, or a combination thereof,
the method comprising
adsorbing the ionic species from the solution by an adsorbent comprising celite, diatomaceous earth, silica, alumina, or a combination thereof;
crystallizing the biphenol dianhydride from the solution;
filtering the solution to remove the ionic species; or
a combination thereof.

5. The method of claim 1, wherein the biphenol dianhydride is an isomer mixture.

6. The method of claim 1, wherein the biphenol dianhydride comprises
less than 25 ppm each of sodium ions, potassium ions, calcium ions, zinc ions, aluminum ions, titanium ions, phosphorus ions, and iron ions;
less than 110 ppm total of sodium ions, potassium ions, calcium ions, zinc ions, aluminum ions, titanium ions, phosphorus ions, and iron ions;
less than 20 ppm each of phosphate ions, sulfate ions, sulfite ions chloride ions, nitrate ions, and nitrite ions; and
less than 50 ppm total of phosphate ions, sulfate ions, chloride ions, nitrate ions, and nitrite ions.

7. A biphenol dianhydride made by the method of claim 1.

* * * * *